United States Patent [19]
Birnbaum et al.

[11] Patent Number: 5,958,416
[45] Date of Patent: Sep. 28, 1999

[54] HEAT SHOCK PROTEIN PEPTIDES AND METHODS FOR MODULATING AUTOIMMUNE CENTRAL NERVOUS SYSTEM DISEASE

[75] Inventors: Gary Birnbaum, Excelsior; Linda A. Kotilinek, Minneapolis, both of Minn.; Peter Erich Braun, Montreal, Canada

[73] Assignees: Regents of the University of Minnesota, Minneapolis, Minn.; McGill University, Montreal, Canada

[21] Appl. No.: 08/447,154

[22] Filed: May 23, 1995

Related U.S. Application Data

[63] Continuation-in-part of application No. 08/368,834, Dec. 16, 1994.
[51] Int. Cl.$^6$ ..................................................... A61K 39/02
[52] U.S. Cl. ...................... 424/190.1; 514/903; 514/885; 424/184.1; 530/300; 530/350
[58] Field of Search ..................................... 514/903, 885; 424/184.1, 190.1; 530/300, 350, 328

[56] References Cited

FOREIGN PATENT DOCUMENTS

WO A 94 02509  2/1994  WIPO .

OTHER PUBLICATIONS

Desquenne — Clark et al PNAS 88 (1991) 7219–7223.
Birnbaum et al. Annals of Neurology (1993) 18–24.
Kurihara et al BBRC 152(2) (1988) 837–842.
Birnbaum et al. Neurology 44 (4) PA146.
Weiner et al. Science 259 (1993) 1321–1324.
Neurology, vol. 44, No. 4, Apr. 1994, p. A146, Birnbaum G et al.
Clin. Exp. Immunol., vol. 87, No. 1, 1992, p. 99–104; Yang, X.D. et al.
Human Immunology, vol. 42, Mar. 1995, p. 301–306, Henwood J. et al.
Springer Semin Immunopathol, vol. 17, No. 1, 1995, Germany, pp. 17–118, Birnbaum G. pp. 114–115.
Neurology, vol. 45, No. 4, Apr. 1995, p. a226 Birnbaum G. et al.
Journal of Neuroscience Research, vol. 44, No. 4, May 15, 1996, USA pp. 381–396, Birnbaum G. et al.

*Primary Examiner*—Anthony C. Caputa
*Assistant Examiner*—Heather A. Bakalyar
*Attorney, Agent, or Firm*—Merchant, Gould, Smith, Edell, Welter & Schmidt, P.A.

[57] ABSTRACT

The invention provides for peptides and methods of using peptides to block or inhibit a pathogenic autoimmune response to central nervous system components. One class of peptides are antigens derived from mycobacterial heat shock proteins and may immunologically cross-react with or are homologous to myelin components. The peptides can also be derived from myelin components such as 2',3' cyclic nucleotide phosphodiesterase and immunologically cross-react with and/or are homologous to mycobacterial heat shock proteins. A method of the invention involves administering a pharmaceutical composition including at least one peptide to an animal in an amount effective to block or inhibit a pathogenic autoimmune response to central nervous system components. The peptides are useful for the prevention, and treatment of autoimmune inflammatory central nervous system disease.

15 Claims, 15 Drawing Sheets

FIG. 4

Sequence Similarity Between The Epitope of HSP65 Recognized by IIH9 and A Peptide of CNP

```
              115                    123
IIH9 Epitope  Leu-Lys-Arg-Gly-Ile-Glu-Lys-Ala-Val  (SEQ ID NO:2)
              |   |       |   |   |   |
CNP           Leu-Lys-Pro-Gly-Leu-Glu-Lys-Asp-Phe  (SEQ ID NO:1)
              156                    164
```

FIG. 9

Sequence of M. leprae 65kD Protein

```
                                                  MAKTIAYDEEARR
                                                  ①
GLERGLNSLADAVKVTLGPKGRNVVLEKKWGAPTITNDGVSIAKEIELEDPYEKIGAELV
KEVAKKTDDVAGDGTTTATVLAQALVKEGLRNVAAGANPLGLKRGIEKAVDKVTETLLKD
AKEVETKEUIAATAAISAGDQSIGDLIAEAMDKVGNEGVITVEESNTFGLQLELTEGMRF
DKGYISGYFVTDAERQEAVLEEPYILLVSSKVSTVKDLLPLLEKVIQAGKSLLIIAEDVE
GEALSTLVVNKIRGTFKSVAVKAPGFGDRRKAMLQDMAILTGAQVISEEVGLTLENTDLS
LLGKARKVVMTKDETTIVEGAGDTDAIAGRVAQIRTEIENSDSDYDREKLQERLAKLAGG
VAVIKAGAATEVELKERKHRIEDAVRNAKAAVEEGIVAGGGVTLLQAAPALDKLKLTGDE
ATGANIVKVALEAPLKQIAENSGMEPGVVAEKVRNLSVGHGLNAATGEYEDLLKAGVADP
VKVTRSALQNAASIAGLFLTTEAVVADKPEKTAAPASDPTGGMGGMDF
```

(SEQ. ID NO: 20)

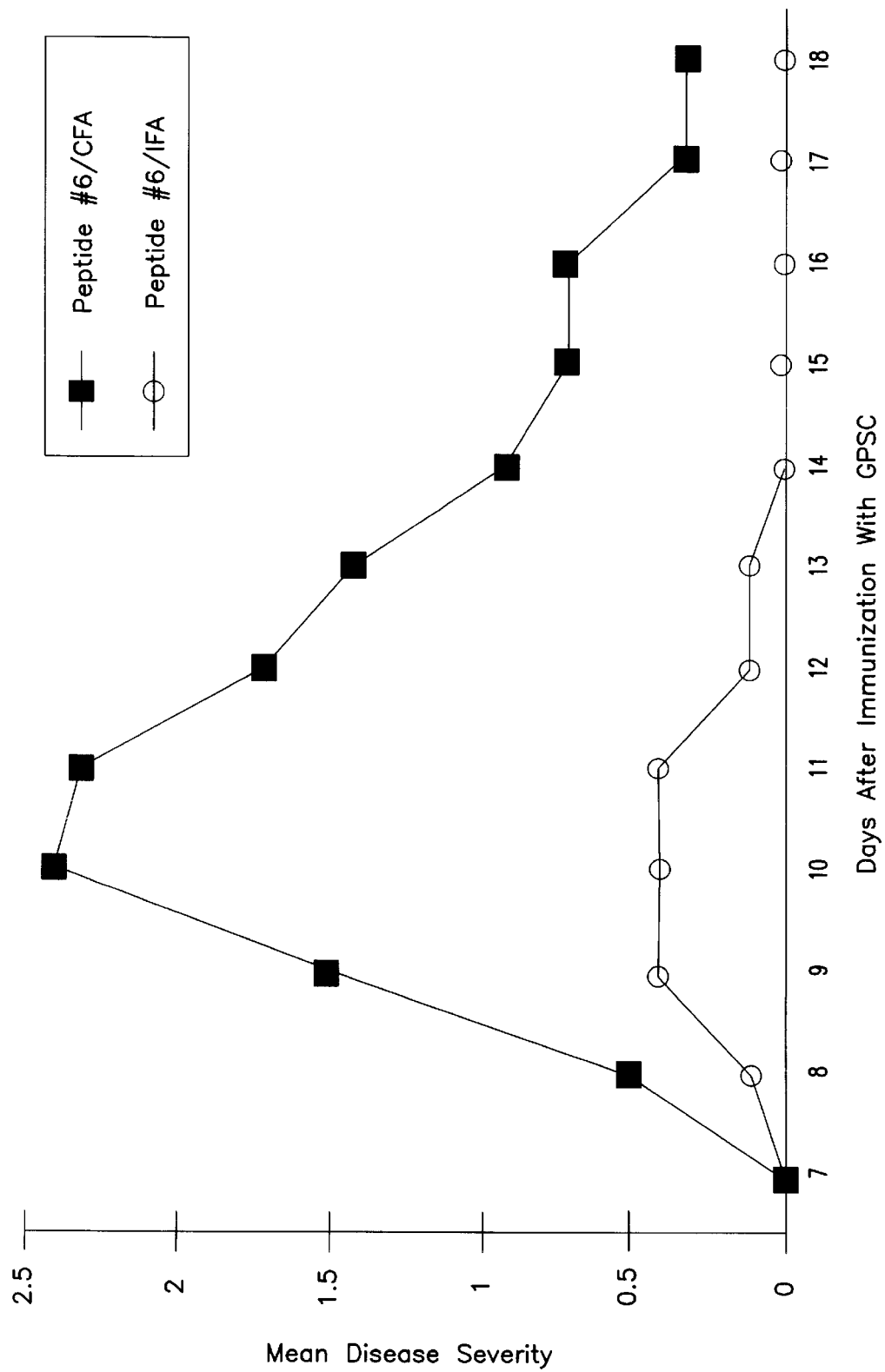

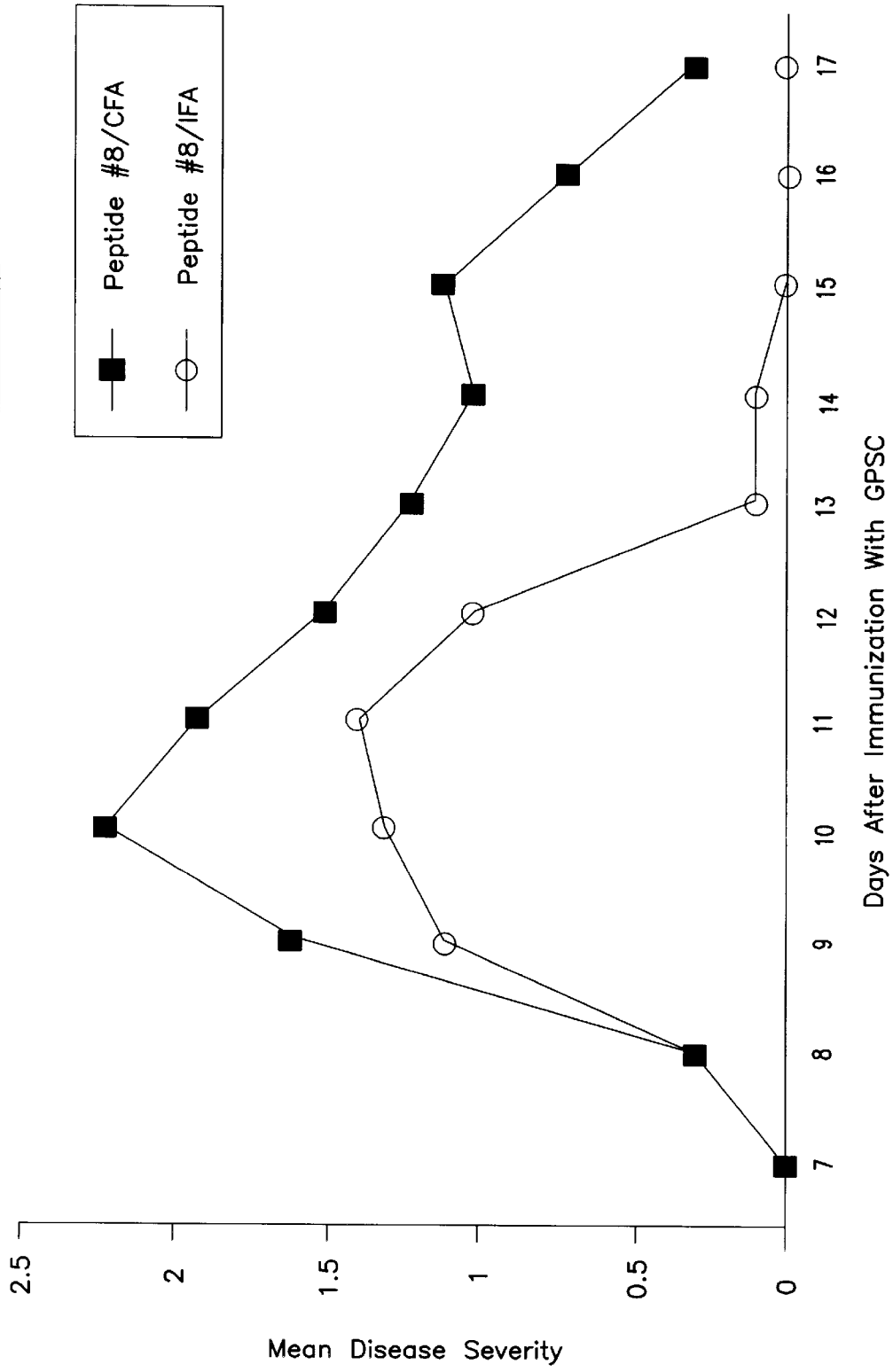

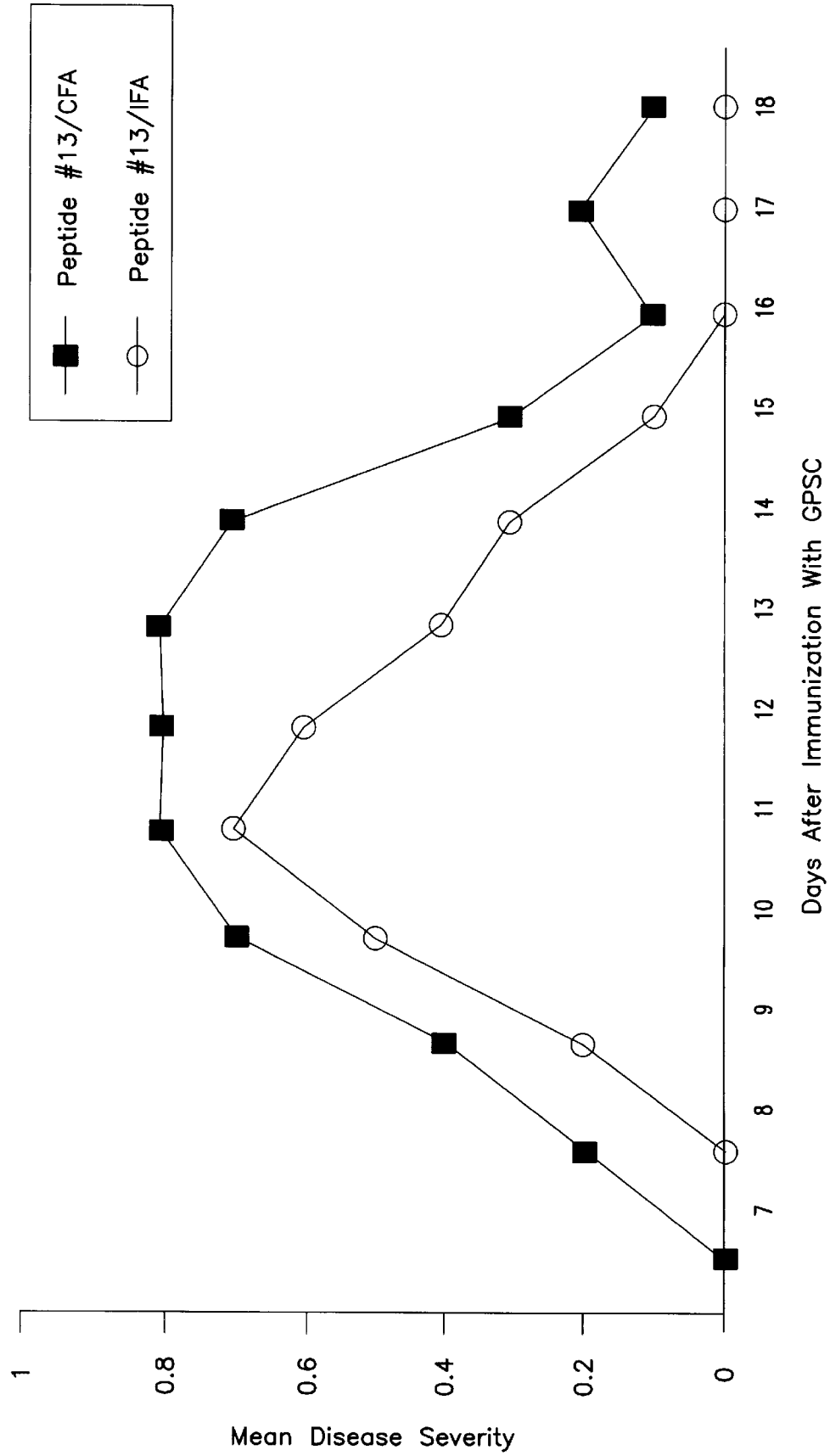

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Leu Lys Pro Gly Leu Glu Lys Asp Phe
1               5

(2) INFORMATION FOR SEQ ID NO:2:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Leu Lys Arg Gly Ile Glu Lys Ala Val
1               5

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Leu Ser Leu Ala Lys Lys Met Glu Val Lys Ala Ile Phe Thr
1               5                   10                  15
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Lys Leu Ser Ile Ser Ala Leu Phe Val Thr Pro Lys Thr Ala Gly
1               5                   10                  15
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ser Thr Leu Ala Arg Leu Ile Val Glu Lys Tyr His Asn Gly Thr
1               5                   10                  15
```

(2) INFORMATION FOR SEQ ID NO:6:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Ala His Val Thr Leu Gly Cys Ala Ala Asp Val Gln Pro
1               5                   10
```

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Asp Leu Lys Lys Leu Lys Pro Gly Leu Glu Lys Asp Phe Leu Pro
1               5                   10                  15
```

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Lys Leu Tyr Ser Leu Gly Lys Gly Arg Trp Met Leu Ser Leu Ala Lys
1               5                   10                  15
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ala Ala Asp Val Gln Pro Val Gln Thr Gly Leu Asp Leu Leu Glu
1               5                   10                  15
```

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Leu Leu Ile Ile Ala Glu Asp Val Glu Gly Glu Ala Leu Ser Thr
1               5                   10                  15
```

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Lys Gly Tyr Ile Ser Gly Tyr Phe Val Thr Asp Ala Glu Arg Gln
1               5                   10                  15
```

(2) INFORMATION FOR SEQ ID NO:12:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Val Arg Asn Ala Lys Ala Ala Val Glu Glu Gly Ile Val Ala Gly
1               5                   10                  15
```

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Gly Gly Val Thr Leu Leu Gln Ala Ala Pro Ala Leu Asp
1               5                   10
```

(2) INFORMATION FOR SEQ ID NO:14:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Asn Pro Leu Gly Leu Lys Arg Gly Ile Glu Lys Ala Val Asp Lys
1               5                   10                  15
```

(2) INFORMATION FOR SEQ ID NO:15:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Asp Leu Ser Leu Leu Gly Lys Ala Arg Lys Val Val Met Thr Lys Asp
1               5                   10                  15
```

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Leu Leu Val Ser Ser Lys Val Ser Thr Val Lys Asp Leu Leu Pro
1               5                   10                  15
```

(2) INFORMATION FOR SEQ ID NO:17:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Leu Lys Lys Leu Lys Pro Gly Leu Glu Lys Asp Phe
1               5                   10
```

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Val Ala Val Lys Ala Pro Gly Phe Gly Asp Arg Arg Lys Ala Met
 1               5                  10                  15
```

(2) INFORMATION FOR SEQ ID NO:19:

(i) SEQUENCE CHARACTERISTICS:
        (A) LENGTH: 541 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Met Ala Lys Thr Ile Ala Tyr Asp Glu Glu Ala Arg Arg Gly Leu Glu
 1               5                  10                  15

Arg Gly Leu Asn Ser Leu Ala Asp Ala Val Lys Val Thr Leu Gly Pro
                20                  25                  30

Lys Gly Arg Asn Val Val Leu Glu Lys Lys Trp Gly Ala Pro Thr Ile
            35                  40                  45

Thr Asn Asp Gly Val Ser Ile Ala Lys Glu Ile Glu Leu Glu Asp Pro
    50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Lys Glu Gly Leu Arg Asn Val Ala Ala Gly Ala Asn Pro
            100                 105                 110

Leu Gly Leu Lys Arg Gly Ile Glu Lys Ala Val Asp Lys Val Thr Glu
    115                 120                 125

Thr Leu Leu Lys Asp Ala Lys Glu Val Glu Thr Lys Glu Gln Ile Ala
130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Ala Glu Arg
    195                 200                 205

Gln Glu Ala Val Leu Glu Glu Pro Tyr Ile Leu Leu Val Ser Ser Lys
210                 215                 220

Val Ser Thr Val Lys Asp Leu Leu Pro Leu Leu Glu Lys Val Ile Gln
225                 230                 235                 240

Ala Gly Lys Ser Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270
```

```
Ala Val Lys Ala Pro Gly Phe Gly Asp Arg Arg Lys Ala Met Leu Gln
        275                 280                 285

Asp Met Ala Ile Leu Thr Gly Ala Gln Val Ile Ser Glu Glu Val Gly
        290                 295                 300

Leu Thr Leu Glu Asn Thr Asp Leu Ser Leu Leu Gly Lys Ala Arg Lys
305                 310                 315                 320

Val Val Met Thr Lys Asp Glu Thr Thr Ile Val Glu Gly Ala Gly Asp
                325                 330                 335

Thr Asp Ala Ile Ala Gly Arg Val Ala Gln Ile Arg Thr Glu Ile Glu
                340                 345                 350

Asn Ser Asp Ser Asp Tyr Asp Arg Glu Lys Leu Gln Glu Arg Leu Ala
            355                 360                 365

Lys Leu Ala Gly Gly Val Ala Val Ile Lys Ala Gly Ala Ala Thr Glu
        370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Gly Val Thr
                405                 410                 415

Leu Leu Gln Ala Ala Pro Ala Leu Asp Lys Leu Lys Leu Thr Gly Asp
                420                 425                 430

Glu Ala Thr Gly Ala Asn Ile Val Lys Val Ala Leu Glu Ala Pro Leu
        435                 440                 445

Lys Gln Ile Ala Phe Asn Ser Gly Met Glu Pro Gly Val Val Ala Glu
        450                 455                 460

Lys Val Arg Asn Leu Ser Val Gly His Gly Leu Asn Ala Ala Thr Gly
465                 470                 475                 480

Glu Tyr Glu Asp Leu Leu Lys Ala Gly Val Ala Asp Pro Val Lys Val
                485                 490                 495

Thr Arg Ser Ala Leu Gln Asn Ala Ala Ser Ile Ala Gly Leu Phe Leu
                500                 505                 510

Thr Thr Glu Ala Val Val Ala Asp Lys Pro Glu Lys Thr Ala Ala Pro
        515                 520                 525

Ala Ser Asp Pro Thr Gly Gly Met Gly Gly Met Asp Phe
        530                 535                 540
```

HEAT SHOCK PROTEIN PEPTIDES AND METHODS FOR MODULATING AUTOIMMUNE CENTRAL NERVOUS SYSTEM DISEASE

This application is a continuation-in-part of application Ser. No. 08/368,834 filed Feb. 16, 1994.

STATEMENT REGARDING FEDERALLY-FUNDED AND SPONSORED RESEARCH

This invention was made with government support from the National Institute of Health under Contract No. 1R01NS29691. The government may have certain rights in this invention.

BACKGROUND OF THE INVENTION

Heat shock proteins (hsp), or stress proteins, are families of essential proteins present in almost all prokaryotic and eukaryotic cells (Morimoto et al., *Stress Proteins in Biology & Medicine*, Cold Spring Harbor, N.Y. (1990)). Heat shock proteins are essential for normal cell functions and are expressed both constitutively and in increased amounts when cells are stressed in a variety of ways. Some examples of stresses that increase expression of hsp are heat, viral infection of cells, anoxia, and exposure to certain cytokines, such as tumor necrosis factor and interferon-gamma.

They are the immunodominant antigens of many bacteria and parasites, both pathogenic and non-pathogenic, and immune responses to these proteins are ubiquitous in normal individuals (Monk et al., *J. Immunol.*, 143:2844 (1989)). Despite their ubiquity, immune responses to hsp may be important in several human and experimental diseases. (Elias et al., *PNAS*, 88:3088 (1991); Van Eden et al., *Curr Top Microbial Immuno.*, 147:27 (1989)). There are several examples of human and experimental autoimmune diseases associated with immune responses to hsp, especially HSP65 (Van Eden, W., *Apmis*, 98:383–394 (1990); Gaston, *Semn. Immunol.*, 3:35–42 (1991)). These diseases include rheumatoid arthritis, type 1 diabetes mellitus, rheumatic diseases and systemic lupus erythmatosis. (Gaston, *J. Semn. Immunol.*, 3:35–42 (1991)).

Several facts about hsp support their potential importance in the development of autoimmune diseases. (Jones et al., *Immunol. Today*, 14:115 (1993)). First, hsp are phylogenetically conserved. Thus, there is greater than 50% sequence homology between certain prokaryotic hsp and those of mammalian cells. Second, hsp are the immunodominant antigens for many infectious agents, including bacteria, mycobacteria, and parasites. The resulting strong immune response to these agents' hsp have the potential either to cross-react with the host's hsp, or with normal tissue components of the host.

It is unexpected that a universal immune response to a common family of proteins can be associated with diseases states in particular individuals. One way to reconcile this phenomenon is to postulate individual differences in the patterns of immune response to these proteins. This phenomenon is well illustrated in persons with leprosy. All infected individuals mount immune responses to the hsp of *Mycobacterium leprae* (*M. leprae*). However, some persons develop tuberculoid leprosy while others manifest the lepromatous form of the disease (de Vries, R. Am. J. Rop. Med. Hyg44(4Pt2):4–11(1991)). While the reasons for such differences are not known, several factors are important, especially the major histocompatibility complex (MHC) phenotype of the individual (Ottenhoff et al., *Int. J. Lepr. Other Mycobact. Dis.*, 55:261 (1987)).

In addition, recent observations in several animal models indicate that autoimmune diseases are dependent upon the presence of immune responses to environmental infectious agents (Goverman et al., *Cell*, 72:551 (1993); Kuhn et al., *Cell*, 75:263 (1993)). Inpersons with multiple sclerosis (MS), a chronic inflammatory disease of the central nervous system (CNS), attacks of presumed autoimmune demyelination frequently follow acute viral and bacterial infections (Sibley et al., *Lancet*, 1:1313 (1985)).

An environmental event is important for the development of MS. This is best demonstrated by the geographic distribution of the disease, which increases in frequency with distance from the equator and by migration studies which suggest that persons leaving a region of particular risk for MS prior to puberty acquire the risk of the area to which they move. Those leaving after puberty take with them the risk inherent in their original geographic location. The nature of this early environmental event is not known, but pre-pubertal exposure to an infectious agent is one possibility (Alter et al., *Neurology*, 36:1386 (1986)). Bacterial and viral flora change as one approaches the equator supporting the concept that the geographically specific early event involved in MS susceptibility is an infectious one (Barlow, J. S.; J. Chron. Dis.; 21:265; 1968).

As noted above, infections are associated with exacerbations of disease. (Sibley et al., *Lancet*, 1:1313 (1985)). Such attacks can occur days to weeks after the acute event, usually a virus infection, and thus are not directly related to fever and acute phase reactants.

There are several possible mechanisms by which an infection can trigger a presumed autoimmune event. Cytokine levels increase during an infection and these could activate quiescent, anti-myelin specific T cells present in the CNS. An immune response to bacterial or viral-induced hsp could occur during the infection. This response may cross-react with heat shock proteins expressed in the CNS.

Thus, there is a need to identify epitopes on heat shock proteins from infectious agents that cross-react with autoantigens such as those associated with myelin since immune responses to such epitopes may trigger autoimmune diseases. There also is a need to develop methods for modulating immune responses to epitopes on heat shock proteins that are cross-reactive with autoantigens to ameliorate or prevent autoimmune diseases.

SUMMARY OF THE INVENTION

The invention provides for peptides and methods of using peptides to block or inhibit a pathogenic autoimmune response to central nervous system components. The peptides and methods are useful diagnostically to screen peptide or peptide analogs that can inhibit the pathogenic immune response, to monitor efficacy of therapeutic use and to identify other reagents that may be effective to inhibit the pathogenic autoimmune response. The peptides and methods of the invention are useful therapeutically to treat, prevent or ameliorate symptoms of autoimmune central nervous system disease.

The peptides of the invention include those derived from mycobacterial heat shock proteins, preferably from mycobacterial HSP65.

One class of peptides from HSP65 immunologically cross-react with or share homology with an autoantigen component of myelin, preferably 2',3' cyclic nucleotide 3' phosphodiesterase (CNP). Peptides of the invention also include peptides derived from CNP and that cross-react with or are homologous to HSP65. CNP has not been previously identified as an important antigen in the development of allergic encephalomyelitis. The preferred peptide has a sequence that includes a sequence that corresponds to amino acids 176 to 184 of CNP isoform 2.

A second class of peptides are those derived from HSP65 and that do not cross-react with CNP. These peptides may cross-react with other self components such as human hsp or myelin proteins other than CNP. These peptides form all or a part of T cell epitopes and preferentially stimulate a specific response in T cells from patients with autoimmune central nervous system disease such as MS.

At least one peptide of the invention is combined with a physiologically acceptable excipient to form a pharmaceutical composition. The peptide is one that can modulate, preferably inhibit, an immune response to an autoantigen of the central nervous system. At least one peptide is present in an amount effective to modulate the immune response to the autoantigen. It is preferred that at least one peptide that protects against development of Experimental Allergic Encephalomyelitis (EAE) is a peptide having a sequence corresponding to amino acids 176 to 184 of CNP isoform 2 coupled to KLH, a peptide having a sequence corresponding to amino acids 195 to 209 of *M. leprae* HSP65, a peptide having a sequence corresponding to amino acids 413 to 425 of *M. leprae* HSP65 or a peptide having a sequence corresponding to amino acids 272 to 286 of *M. leprae* HSP65.

The invention also provides a method for inducing tolerance to an autoantigen in the central nervous system. The method involves administering at least one of the peptides in a pharmaceutical composition in an amount effective to tolerize the animal to the peptide and/or an autoantigen, preferably CNP. While not meant to limit the invention it is believed that one way a peptide can block or inhibit a pathogenic immune response is by inducing tolerance to the autoantigen.

The invention also provides methods of treating, preventing or ameliorating symptoms of autoimmune inflammatory central nervous system disease. A patient experiencing symptoms of CNS disease, such as multiple sclerosis, is administered at least one peptide of the invention in a pharmaceutical composition. The patient is administered the pharmaceutical composition in an amount effective to decrease the symptoms of the disease. Preferably that amount is a tolerizing dose so that a pathogenic immune response to autoantigen is inhibited. A preferred method of treatment is to treat patients exhibiting acute exacerbations of the disease with at least one peptide in an amount effective to decrease severity of symptoms and damage.

BRIEF DESCRIPTION OF FIGURES

FIG. 4: Sequence similarity between the epitope of HSP65 recognized by IIH9 and a peptide of CNP (SEQ ID Nos. 2 and 1, respectively). The solid vertical bars between amino acids indicate residue identity. The dotted vertical bars represent conservative residue substitutions.

FIG. 9: The sequence of HSP65 from *M. leprae* obtained from GenBank (SEQ ID NO:19).

FIG. 10: Preimmunization with peptide #6 in incomplete Freund's adjuvant protects rats against EAE.

FIG. 11: Preimmunization with peptide #8 in incomplete Freund's adjuvant protects rats against EAE.

FIG. 13: Preimmunization with peptide #13 not coupled to KLH does not protect rats against EAE.

DETAILED DESCRIPTION

Figure 1A:
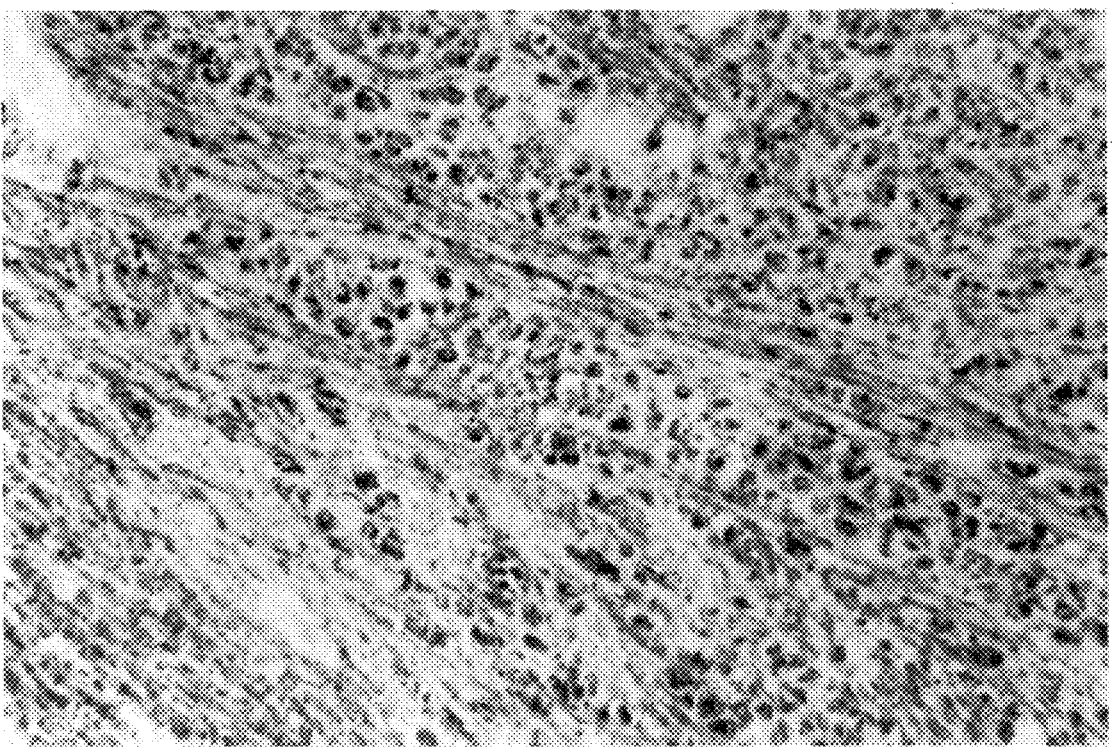
FIGS. 1*a, b*, and *c*: Immunocytochemical staining of human spinal cord. All sections were photographed at a magnification of 250×. The bar on the photomicrographs represents 40 microns. Solid arrows point to myelin sheaths cut in cross sections. Hollow arrows point to myelin sheaths cut longitudinally. 1*a*. Staining with IIH9 antibody. 1*b*. Staining with IIC8 antibody. 1*c*. Staining with rabbit anti-CNP antibody.
Figure 1B:
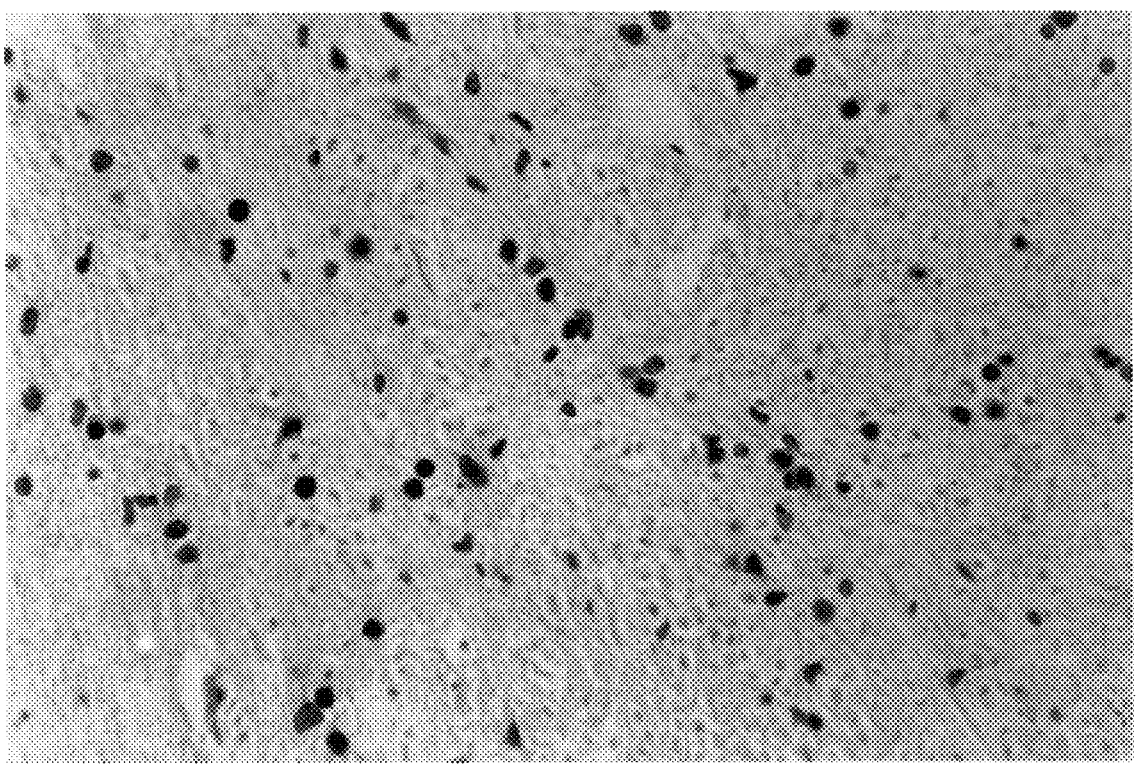

The invention is directed to peptides and methods of using peptides to block or inhibit a pathogenic autoimmune response to components of the central nervous system. The peptides of the invention are derived from or correspond to peptides found in heat shock proteins, preferably mycobacterial HSP65. The peptides are selected initially as all or a portion of an epitope that can stimulate proliferation of normal human T cells. Of those peptides that are epitopes for human T cells, there are two classes of peptides. The first class includes those peptides that are selected because they immunologically cross-react or are homologous to myelin components such as 2',3' cyclic nucleotide phosphodiesterase (CNP) or other myelin proteins. The second class of peptides are those derived from HSP65 and that are selected because they stimulate a specific T cell response in patients with autoimmune central nervous system disease such as MS. The second class of peptides may cross-react with self components. Preferably immunization with peptides of both classes protect against the development or exacerbation of autoimmune central nervous system disease.

The peptides are formulated in pharmaceutical compositions by combining at least one peptide with a pharmaceutically acceptable excipient in an amount effective to modulate an immune response to the peptide and/or myelin. A method of the invention involves administering a pharmaceutical composition including at least one peptide to an animal in an amount effective to block or inhibit a pathogenic autoimmune response to central nervous system components. Another method of the invention involves administering the peptide in an amount effective to tolerize the animal to the peptide and/or myelin after an acute exacerbation of autoimmune central nervous system disease so that the course of the autoimmune central nervous system disease is modulated.

These peptides are useful in pharmaceutical compositions for the prevention and treatment of symptoms of autoimmune central nervous system disease such as multiple sclerosis, acute disseminated encephalitis, and other chronic inflammatory CNS disease. The peptides are also useful for generating antibodies and detecting antibodies to components of myelin. Detection of antibodies to the peptides could be used to monitor the effectiveness of the methods for modulating immune responses such as tolerizing animals to the peptides and/or to myelin components. The peptides are also useful to generate T-lymphocytes specific for the peptides, preferably suppressor T-lymphocytes. Lymphocytes that are specific for the peptide can be used to identify reagents that block or inhibit an immune response to the peptides as well as to monitor the efficacy of modulating immune responses to the peptide such as tolerizing the animal to the peptide and/or to myelin components.

Peptides

Figure 9:
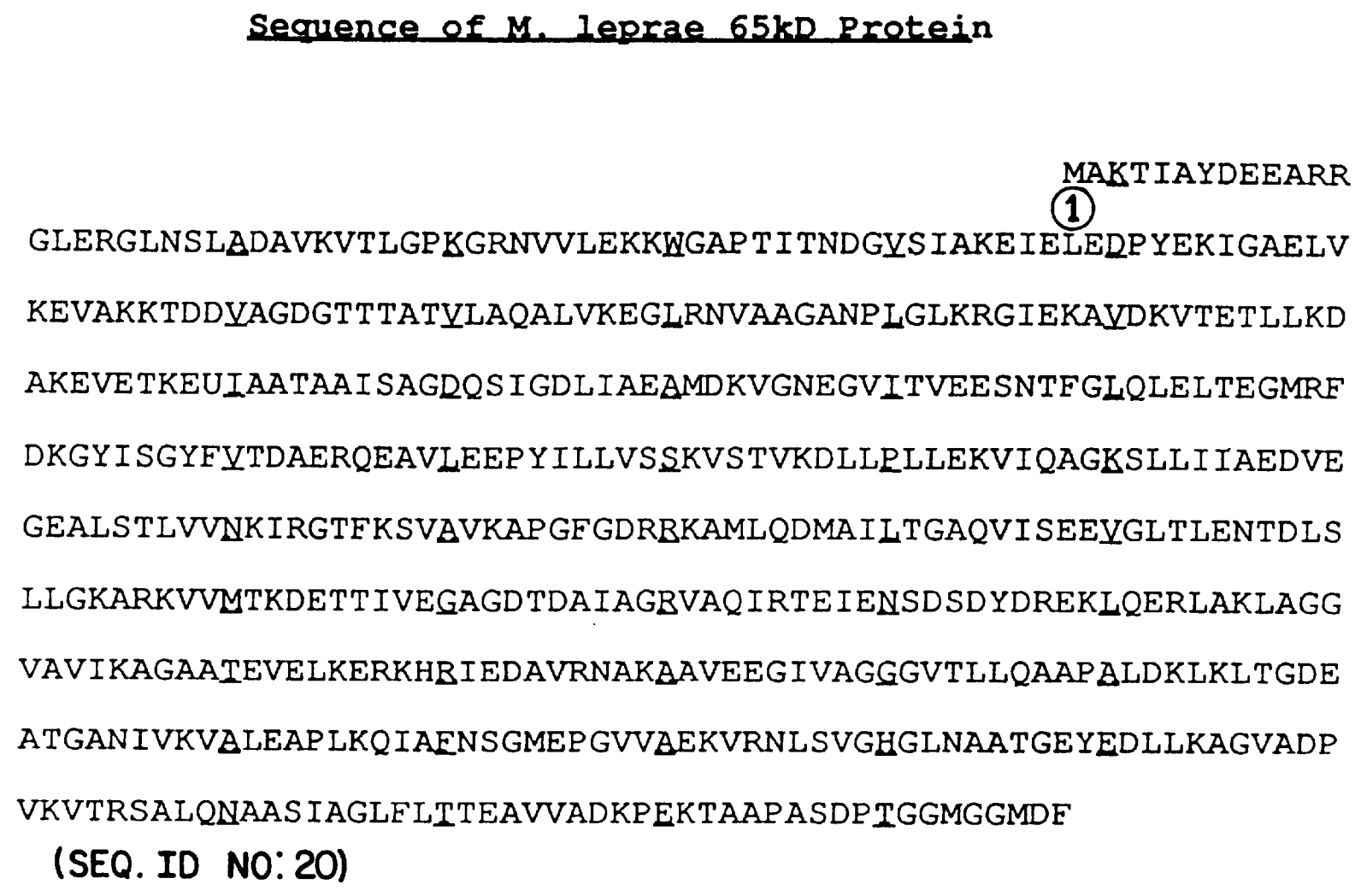

The peptides of the invention are those peptides that can preferably modulate an immune response by blocking or inhibiting a pathogenic autoimmune response to components of the central nervous system such as myelin. The peptides are those that can stimulate a cross-reactive immune response to self components especially myelin components. The peptides are initially selected as all or a portion of epitopes of HSP65 that stimulate proliferation of normal human T cells. The HSP65 is preferably mycobacterial HSP65 and the molecular weight of the protein is determined by SDS PAGE. The especially preferred HSP5 is that derived from *M. leprae* and has a sequence as shown in FIG. 9. Once identified as all or a portion of a T cell epitope, the peptides can be further selected into two classes.

The first class includes peptides derived from HSP65 that immunologically cross-react with or share homology with human myelin components. The preferred myelin component is 2',3' cyclic nucleotide phosphodiesterase (CNP) but others can also be considered such as myelin basic protein, proteolipid protein, and myelin oligodendrocyte glycoprotein.

One way that peptides of class I are identified is by determining whether T cell epitopes of HSP65 share homology with peptides of myelin components such as CNP. Peptides can be derived from either HSP65 or from 2',3' cyclic nucleotide phosphodiesterase. For example, peptides of about 15–20 amino acids that have been identified as T cell epitopes in HSP65 have been screened for homology with peptides in CNP using standard computer analysis using FASTA (publicly available). Once identified as homologous by FASTA, those peptides that have at least 5 identical residues out of 10–15 are selected. Peptides of mycobacterial HSP65 and peptides of CNP that share about 60 to 100% amino acid sequence homology are selected. CNP as a component of myelin has not been previously shown to be important in autoimmune responses.

Homology between the sequences is used to identify and select antigens of the mycobacterial heat shock proteins or myelin components that may stimulate an immune response that is cross-reactive with mycobacterial antigens and/or autoantigens. Homology between amino acid sequences is determined by first comparing the amino acid sequences of two proteins using a computer program FASTA that is publicly available. FASTA identifies peptides that are homologous by identifying residues that are identical and those that have conservative amino acid substitutions when two sequences are compared. Once identified as a homologous peptide by FASTA, a visual comparison is made between the two sequences. In the visual comparison, those peptides that have at least 5 identical residues out of about 10–15 residues are selected. In this manner, the amino acid sequences for T cell epitopes of HSP65 from *M. leprae* were compared to the amino acid sequence for human CNP. Preferably, the peptides selected as homologous have at least 60% residues that are similar, i.e., that are identical or have a conservative substitution. It is preferred that the peptides compared are about 9 to 20 amino acids in length. Of the peptides that are homologous, they preferably have about 60 to 100% homology and more preferably about 70% to 100% homology.

Another way to identify peptides of class I is to determine whether the peptides of mycobacterial heat shock proteins stimulate a cross-reactive immunological response to components of myelin. The peptides identified as cross-reactive may or may not have sequence homology to a known myelin component or self component. The immunological cross-reactivity of the peptides from myelin and mycobacterial heat shock proteins can be determined using standard methods such as the ELISA assay, immunoblot assay, or lymphocyte proliferation assays. A lymphocyte proliferation assay is preferred. In a lymphocyte proliferation assay, it is generally understood by those of skill in the art that a proliferative response to a particular antigen of about 2 to 3 times above control is indicative of a cross-reactive immunological response. In measuring cross-reactivity using antibody reactivity, the responsiveness indicative of cross-reactivity depends on the assay. In general, antibody reactivity of about 2 to 3 times above control is indicative of a cross-reactive antibody response. Several polyclonal and monoclonal antibodies to heat shock proteins are available.

Optionally, peptides of this first class can be further selected based upon the ability to stimulate a specific T cell proliferative response in patients with autoimmune central nervous system disease. It is preferred that the patient has multiple sclerosis but peptides can be selected that stimulate specific responses in lymphocytes in patients with other autoimmune diseases. A specific response of patient's lymphocytes is about a 2–3 fold increase in proliferation over control lymphocytes from patients with other neurological disease.

While not meant to limit the invention, it is believed that T cell responses of patients to the different peptides may vary depending on histocompatibility type. For example, a patient with a known histocompatibility type can be tested with peptides that are selected because they can stimulate a proliferative response in T cells having the particular major histocompatibility antigen of the patient.

For example, peptides selected for treating MS patients may include at least one peptide that stimulates an enhanced response in patients with a DR2 type. Susceptibility to MS in persons of Northern European extraction is associated with HLA-DR2, a Class II MHC molecule. The ability of the peptide to associate with or be presented by DR2 lymphocytes may identify peptides that can protect against or block a pathogenic immune response.

Optionally, the peptides that stimulate an immune response in T cells from patients with autoimmune central nervous system disease can be characterized for the type of T cell response stimulated. It is known to those of skill in the art that the same peptide can evoke different responses in lymphocytes resulting in the secretion of different cytokines.

These responses are defined as a Th1 response and Th2 responses. Th1 cells secrete interleukin 2, interferon gamma and tumor necrosis factor. Th2 cells secrete interleukin 4, interleukin 5 and interleukin 10. Th1 responses are pathogenic responses implicated in persons with MS. Spinal fluids and brains from persons with MS contained increased amounts of Th1 cytokines. Peptides can be identified that induce tolerance inducing Th2 responses rather than pathogenic Th1 responses. The profile of cytokine responses produced can be measured using methods known to those of skill in the art such as ELISPOT assays.

Peptides in class I derived from HSP65, CNP or another myelin component can be further selected by identifying peptides that protect animals against the development of experimental allergic encephalomyelitis (EAE) or ameliorate the symptoms of EAE in animals. Peptides are used to pre-immunize animals and then the animals are challenged with guinea pig spinal cord. Protection against disease is determined by monitoring the severity and onset of the disease.

The preferred way to select and identify peptides useful to treat patients with autoimmune central nervous system disease such as MS is to identify a peptide of HSP65 that stimulates a preferential response or specific response of T cells from MS patients. Those peptides that stimulate a specific response in T cells from MS patients are then further selected for the ability to protect animals against EAE or ameliorate the symptoms of EAE. These peptides are then further selected as peptides that stimulate a Th2 response in MS lymphocytes.

While not meant to limit the invention, it is believed that the mycobacterial heat shock proteins stimulate immune responses that immunologically cross-react with self antigenic components of myelin such as CNP. These cross-reactive immune responses contribute to the damage and development of central nervous system autoimmune disease. Immunization with a peptide derived from CNP can protect against development of allergic encephalomyelitis stimulated by a complex mixture of encephalitogenic antigens in a spinal cord preparation. It is believed that peptides derived from mycobacterial or bacterial heat shock proteins that immunologically cross-react with myelin proteins such as CNP are involved in stimulating an immune response that results in a final common pathway to disease development. Cross-reactive or homologous peptides derived from either CNP or HSP65 can be useful to stimulate an immune response that blocks or inhibits a pathogenic immune response to central nervous system components.

Specific examples of peptides designated as class I include those peptides that have at least 9 amino acids and that correspond to peptides derived from CNP isoform 1 or isoform 2. The cDNA and predicted amino acid sequence of CNP isoform 2 has been published in Gravell et al., *J. Neuroscience Res.*, 38:243–247 (1994) and amino acid number designations for CNP in this application are made by reference to that sequence. However, it will be understood by those of skill in the art that the same or a similar peptide may be identified using different numbers for the amino acid residues. Thus, although this application makes reference to amino acid numbers it is the amino acid sequence that should be compared and not the amino acid number designations as they can change depending on the source of the sequence.

A peptide from CNP isoform 2 identified as immunologically cross-reactive with mycobacterial HSP65 is a peptide including a sequence corresponding to amino acids 176–184:

leu-lys-pro-gly-leu-glu-lys-asp-phe (SEQ ID NO:1)

This peptide immunoreacts with antibodies specific for mycobacterial HSP65 and has about 78% similar or homologous residues to a peptide including the sequence of amino acids corresponding to amino acids 115 to 123 of *M. leprae* HSP65, leu-lys-arg-gly-ile-glu-lys-ala-val (SEQ ID NO:2). Preimmunization with this peptide protects against development of EAE when the peptide is coupled to KLH. This peptide is a B cell epitope when it is not coupled to KLH and does not protect against development of EAE. When the peptide is coupled to KLH it is likely functioning as a T cell epitope.

Other peptides derived from CNP are similar or homologous to peptides of mycobacterial HSP65 as described previously. These peptides are described below. A peptide including or having a sequence corresponding to amino acids 380–394 of CNP isoform 2:

met-leu-ser-leu-ala-lys-lys-met-glu-val-lys-ala-ile-phe-thr (SEQ ID NO:3)

is homologous or similar to a peptide of residues 245–259 (#5) *M. leprae* HSP65 with the sequence shown in Table 1.

A peptide including or having the sequence corresponding to amino acids 282–296 of CNP isoform 2:

lys-leu-ser-ile-ser-ala-leu-phe-val-thr-pro-lys-thr-ala-gly (SEQ ID NO:4)

and is homologous or similar to a peptide having the sequence of amino acids 195–209 (#6) of *M. leprae* HSP65 with the sequence shown in Table 1.

A peptide including or having the sequence corresponding to amino acids 64–78 of CNP isoform 2:

ser-thr-leu-ala-arg-leu-ile-val-glu-lys-tyr-his-asn-gly-thr (SEQ ID NO:5)

and is homologous or similar to a peptide having the sequence of amino acids 398–412 (#7) of *M. leprae* HSP65 with the sequence shown in Table 1.

A peptide including or having the sequence corresponding to amino acids 328–340 of CNP isoform 2:

ala-his-val-thr-leu-gly-cys-ala-ala-asp-val-gln-pro (SEQ ID NO:6)

and is homologous or similar to a peptide having the sequence of amino acids 413–425 (#8) of *M. leprae* HSP65 as shown in Table 1.

A peptide including or having the sequence corresponding to amino acids 172–186 of CNP isoform 2:

asp-leu-lys-lys-leu-lys-pro-gly-leu-glu-lys-asp-phe-leu-pro (SEQ ID NO:7)

and is homologous or similar to a peptide having the sequence of amino acids 111 to 125 (#10) of *M. leprae* HSP65 as shown in Table 1.

A peptide including or having the sequence corresponding to amino acids 370–386 of CNP isoform 2:

lys-leu-tyr-ser-leu-gly-lys-gly-arg-trp-met-leu-ser-leu-ala-lys (SEQ ID NO:8)

and is homologous or similar to a peptide having the sequence of amino acids 311 to 326 (#11) of *M. leprae* HSP65 as shown in Table 1.

A peptide including or having the sequence corresponding to amino acids 335–349 of CNP isoform 2:

ala-ala-asp-val-gln-pro-val-gln-thr-gly-leu-asp-leu-leu-glu (SEQ ID NO:9)

and is homologous or similar to a peptide having the sequence of amino acids 219 to 233 (#12) of *M. leprae* HSP65 as shown in Table 1.

The sequence for HSP65 from *M. leprae* is shown in FIG. 9. This sequence was obtained from Genbank. Peptides of the first class derived from HSP65 either immunologically cross-react with or preferably share about 60 to 100% homology, more preferably about 70–100% with peptides from CNP.

A peptide derived from HSP65 includes a sequence that corresponds to amino acids 115 to 123 when counted from the methionine at position 1 in the sequence shown in FIG. 9. A peptide corresponding to amino acids 115–123 (peptide #13) has the following sequence:

leu-lys-arg-gly-ile-glu-lys-ala-val (SEQ ID NO:2)

Antibodies to this epitope recognize CNP and bind to this component of myelin indicating this epitope is immunologically cross-reactive with CNP. The amino acid sequence also shares about 78% sequence homology with a peptide derived from CNP corresponding to amino acids 176 to 184 of CNP isoform 2. When this peptide is not coupled to KLH and is used to preimmunize rats, the rats are not protected from EAE. While not meant to limit the invention it is believed that when this peptide is not coupled to a carrier molecule such as KLH, it is a B cell epitope and not a T cell epitope, and therefore does not stimulate a protective or blocking T cell response.

Another peptide corresponds to amino acids 311–326 of M. leprae HSP65 and has the following sequence:

asp-leu-ser-leu-leu-gly-lys-ala-arg-lys-val-val-met-thr-lys-asp. (SEQ ID NO:15)

Other peptides derived from mycobacterial HSP65 have been identified as all or a portion of T cell epitopes and share about 60 to 100% homology with peptides derived from CNP. These peptides are also known to stimulate T cell proliferative responses in some MS patients. The peptides are shown in Table 1:

TABLE 1

| No. | M. Leprae Peptide Sequence | Corresponding Amino Acid Nos. |
|---|---|---|
| 5 | leu-leu-ile-ile-ala-glu-asp-val-glu-gly-glu-ala-leu-ser-thr- (SEQ ID NO:10) | 245–259 |
| 6 | lys-gly-tyr-ile-ser-gly-tyr-phe-val-thr-asp-ala-glu-arg-gln (SEQ ID NO:11) | 195–209 |
| 7 | val-arg-asn-ala-lys-ala-ala-val-glu-glu-gly-ile-val-ala-gly (SEQ ID NO:12) | 398–412 |
| 8 | gly-gly-val-thr-leu-leu-gln-ala-ala-pro-ala-leu-asp (SEQ ID NO:13) | 413–425 |
| 10 | asn-pro-leu-gly-leu-lys-arg-gly-ile-glu-lys-ala-val-asp-lys (SEQ ID NO:14) | 111–125 |
| 11 | asp-leu-ser-leu-leu-gly-lys-ala-arg-lys-val-val-met-thr-lys-asp (SEQ ID NO:15) | 311–326 |
| 12 | leu-leu-val-ser-ser-lys-val-ser-thr-val-lys-asp-leu-leu-pro (SEQ ID NO:16) | 219–233 |
| 13 | leu-lys-arg-gly-ile-glu-lys-ala-val (SEQ ID NO:2) | 115–123 |

Peptides including or having an amino acid sequence corresponding to the sequence of amino acids as shown in Table 1 for amino acids 245–259, 195–209, 398–412, 413–425, 111–125, 311–326 and 219–233 of M. leprae HSP65 are also peptides included in the first class of peptides.

Several of these peptides have been shown to confer a protective response against development of EAE. These peptides were not coupled to a carrier molecule and were injected into rats in incomplete Freund's adjuvant. Peptide #6 and peptide #8 did protect against or decrease the symptoms of EAE. Preimmunization with peptide #13 did not result in protection against EAE but the peptide was not coupled to KLH and therefore may have functioned as a B cell epitope.

Some of these peptides were further tested for stimulation of T cell responses of MS patients. Peptides 5, 6, 7, 8, 9, 10, 11 and 12 were tested the ability to stimulate T cell responses from MS and other neurological disease patients (OND). Peptides 5, 6, 9 and 12 elicited specific T cell proliferative responses in some MS patients compared with OND patients. Peptides 5 and 9 stimulated enhanced T cell proliferative responses in CSF cells from MS patients compared with control OND patients.

A second class of peptides are also derived from mycobacterial heat shock proteins, preferably HSP65 from M. leprae. These peptides correspond to all or a portion of described T cell epitopes and are further selected for the ability to stimulate T cell responses in MS patients. T cell epitopes of HSP65 have been described in Pervin et al., J. Immunol., 151:2273 (1993) and Lamb et al., EMBO, 6:1245 (1987). These peptides may, but are not known to be cross-reactive with CNP. They also may cross-react with other myelin components or self components such as human heat shock proteins. Peptides derived from HSP65 that represent all or a portion of a T cell epitope can be screened for stimulation of T cells of patients with central nervous system autoimmune disease in a lymphocyte proliferation assay. Those peptides that stimulate T cells from MS patients about 2 to 3 fold above control levels and do not stimulate response in patients with other neurological disease are those selected in the second class of peptides of the invention. These peptides represent epitopes that correlate with a specific disease.

A screening assay for identifying peptides that elicit a specific or enhanced T cell response from patients with central nervous system autoimmune disease is as follows. Short term T lymphocyte lines are established from peripheral blood or cerebrospinal fluid obtained from patients by incubation first with HSP65 derived from M. leprae then with phytohemagglutinin-P and interleukin 2. After about 15–20 days in culture the cells are incubated with 5–15 micrograms of the peptide for 48 hours. Cell proliferation is measured using a $H^3$ thymidine incorporation assay. The control is cells cultured without peptide or with a non-HSP peptide. A response of greater than 2 to 3 fold over control indicates a T cell response to the peptide.

Optionally, the peptides of the second class can be further selected because of the ability to stimulate a proliferative response of T cells from patients having a particular HLA type. Susceptibility to different autoimmune diseases are associated with particular HLA types. For example, susceptibility to MS in persons of Northern European origin is associated with HLA-DR2, Class II MHC molecules. Peptides selected for treating MS patients may include at least one peptide that stimulates an enhanced response of lymphocytes from patients with the DR2 HLA type.

Optionally, the peptides that stimulate an immune response in T cells from patients with autoimmune central nervous system disease can be characterized for the type of T cells stimulated. It is known to those of skill in the art that the same peptide can evoke a different response in lymphocytes that result in the secretion of different cytokines. These responses are defined as a Th1 response or Th2 response. Th1 cells secrete interleukin 3, interferon gamma and tumor necrosis factor. Th1 responses are pathogenic responses implicated in persons with MS. Th2 cells secrete interleukin 4, interleukin 5 and interleukin 10. Peptides identified that induce tolerance inducing Th2 responses are selected. The profile of cytokines released by stimulated T cells can be measured using standard methods.

A preferred method of selecting peptides is as follows. Peptides selected as all or a portion of normal human T cell epitopes are screened for stimulating a specific or enhanced T cell response in patients with MS. Peptides are also selected that protect against the development of EAE or decrease the symptoms of EAE. Finally, peptides that stimulate a Th2 response of MS patients lymphocytes are selected.

A specific example of a peptide that is derived from HSP65 but is not cross-reactive with CNP is a peptide that corresponds to amino acids 272 to 286 of *M. leprae* HSP65 (peptide #9) and has an amino acid sequence:

val-ala-val-lys-ala-pro-gly-phe-gly-asp-arg-arg-lys-ala-met (SEQ ID NO:18).

This peptide is a portion of a T cell epitope for normal human T cells and also stimulates an enhanced T cell response in MS patients compared with patients with other neurological disease. This peptide does not share homology with CNP. Preimmunization with this peptide protects rats against the development of EAE.

Both classes of peptides are also those that stimulate a protective or blocking immune response to the development of autoimmune central nervous system disease. Peptides can be examined for a protective effect using an in vitro assay to see whether an incubation with the peptides can modify T cell responses to myelin components. Alternatively, the peptides can be used to immunize animals and ameliorate, delay or prevent the development of EAE.

The peptides of the invention preferably are about 4 to 20 amino acids long, and more preferably about 9 to 15 amino acids long. It is known to those of skill in the art that in order for an epitope to stimulate a specific T cell response it is preferable to have at least 8–12 amino acids. It is especially preferred that the peptide be about 9 to 15 amino acids to ensure proper folding and presentation of the epitope. Peptides larger than about 20 amino acids may be processed differently, and thus may not elicit a cross-reactive or protective immune response.

Peptides within the scope of the invention are also peptide analogs. Peptide analogs include peptides derived from human CNP that preferably share about 60 to 100 percent homology with mycobacterial heat shock proteins, and that have at least one amino acid substitution. Peptide analogs can also be derived from peptides derived from *M. leprae* HSP65 that have at least one amino acid substitution, and that have about 60 to 100% homology with CNP and preferably immunologically cross-react with CNP. It is also preferred that the substitutions increase the homology between the peptides derived from CNP and mycobacteria HSP65. Peptide analogs also include peptides of the second class of peptides with at least one amino acid substitution. The peptides of the second class are derived from HSP65 and stimulate T cells from patients with central nervous system autoimmune disease such as MS. Such peptides may cross-react with myelin proteins other than CNP.

One way that the amino acids that can be substituted in a particular peptide can be identified is by comparing the amino acid sequence of the two peptides, one from CNP and the homologous peptide from HSP65. For example, peptide 115 to 123 of *M. leprae* HSP65 is cross-reactive with CNP peptide 176 to 184. A comparison of these sequences is shown below:

This comparison shows that nonconservative amino acid substitutions can be made at the residues 117 of HSP65 or 178 of CNP and at residues 122 of HSP65 or 183 of CNP. Conservative substitutions can be made at residues 119 of HSP65 or 180 of CNP and at residue 123 of HSP65 or 184 of CNP.

Peptide analogs of the peptides of class II are preferably those that do not change the ability of the peptide to interact with T cell receptors or MHC antigen binding groove and/or to stimulate a protective or blocking immune response. The substitutions are also preferably conservative amino acid substitutions and have been described by Dayhoff in the "Atlas of Protein Sequence and Structure," 5, (1978) and Argos in *EMBO J.*, 8, 779 (1989). The substitutions in the peptide are also preferably those that do not alter the amphipathic regions of the peptide, whether the sequence forms an α helical structure or β sheet as described in Berzofsky et al., *PNAS* 82:7048 (1985).

A pharmaceutical composition of the invention includes at least one peptide that can generate an immune response that blocks or inhibits a pathogenic autoimmune response to central nervous system components. The composition can include more than one peptide as well as peptide analogs as described herein. The composition preferably includes about 1 to 20 different peptide antigens, and more preferably 1–5 different peptide antigens. It is preferred that any combination of peptides includes at least one peptide that protects against the development of EAE such as peptide #6 (see Table 1), peptide #8 (see Table 1), CNP peptide corresponding to amino acids 176 to 184 coupled to KLH, or peptide #9 corresponding to amino acids 272 to 286 of *M. leprae* HSP65. More than 1 peptide may enhance effectiveness, especially if the response to some peptides is MHC restricted. The peptides can be derived from CNP or HSP65 or peptide analogs thereof or can be derived from other components of myelin. Peptides derived from human CNP and that may immunologically cross-react and/or share homology with heat shock proteins are preferably combined in amounts effective to tolerize the animal to antigens of CNP and/or other myelin components. Peptides derived from mycobacterial HSP65 are preferably combined in amounts effective to tolerize the animal to antigens of mycobacterial heat shock proteins, CNP and other myelin components or other self components.

A peptide of the invention can also be combined with other therapeutic agents used to treat, ameliorate, or prevent symptoms of autoimmune central nervous system disease such as occurs in multiple sclerosis. For example, the peptides of the inventions could be combined with peptides derived from myelin basic protein and/or proteolipid protein (PLP) and that do not immunologically cross-react with mycobacterial heat shock proteins. These combinations of peptides are preferably administered in amounts that tolerize the animal to components of myelin such as myelin basic protein, proteolipid protein and CNP.

The peptides of the invention can also be coupled or attached to a carrier molecule. Preferably peptides that function as B cell epitopes are attached to carrier molecules.

```
HSP65       Leu-Lys-Arg-Gly-Ile-Glu-Lys-Ala-Val(SEQ ID NO:2)
sequence

CNP sequence Leu-Lys-Pro-Gly-Leu-Glu-Lys-Asp-Phe(SEQ ID NO:1)
              *   *       *   □   *   *       □
* - identical residues
□ - conservative substitutions
```

The peptide can be attached to a carrier molecule covalently or noncovalently but sufficiently so that the peptide is not readily disassociated when it is administered to an animal. The attachment is preferably a covalent attachment to a molecule such as bovine albumin (BSA), keyhole limpet hemocyanin (KLH), and isologous IgG. The carrier molecule is preferably selected to enhance the ability of the peptide to tolerize the animal to self antigens of myelin. The peptide is preferably coupled to the carrier in amounts effective to induce tolerance. Coupling methods for attaching peptides to different types of carrier molecules are known to those of skill in the art as well as measuring the amount of peptide attached per carrier molecule.

The peptides of the invention can be prepared using automated synthesis or by recombinant methods. The gene for rat CNP isoform 1 has been cloned and expressed in baculovirus vector as described in Cox et al. *J. Neurosci. Res.,* 39:513 (1994). The cDNA for rat CNP isoform 2 has been cloned and sequenced as described in Gravel et al., *J. Neurosci. Res.,* 38:243 (1994). Recombinant peptides can be prepared by subcloning the appropriate region of the gene or by other methods known to those of skill in the art. Peptide analogs can be formed synthetically and by altering the gene sequence. The peptides are isolated using standard methods.

Once the peptides are prepared, at least one peptide is combined with a pharmaceutically acceptable excipient to form a composition. Pharmaceutically acceptable excipients are known to those of skill in the art and include aqueous solutions such as water, saline, Ringer's solution, and phosphate buffered saline.

The peptide can be present in a variety of forms such as liposomes, capsule tablets, suppositories, capsules made of gelatin or in a form suitable for delivery via an epidermal patch or implantable pump.

The composition may optionally include an adjuvant. Adjuvants are known to those of skill in the art and include complete Freund's adjuvant and incomplete Freund's adjuvant.

The peptides are present in an amount effective to modulate an immune response preferably to self antigens. The amount of the peptide preferably is that amount that blocks or inhibits a pathogenic autoimmune response. One way the pathogenic immune response can be blocked is by inducing immunologic tolerance to the peptide, so an effective amount is that amount that tolerizes the animal to the peptide and/or HSP65 or myelin components. Preferably tolerance is established to the peptide as well as to at least one myelin component.

Routes of administration, doses and other factors that affect tolerance are known to those of skill in the art. Tolerance can be established using a variety of routes of administration including parenteral, intraperitoneal, subcutaneous, intramuscular, inhalation or oral routes of administration. Tolerance can be established as low dose or high dose tolerance. For high dose tolerance typically about 5 to 20 fold more peptide is administered.

Tolerance can be induced at a low dose of 1 ng to 100 mg/Kg body weight and more preferably 10 $\mu$g to 10 mg/Kg body weight. For high dose tolerance, 5 ng to 100 mg/Kg and more preferably 20 $\mu$g to 50 mg/Kg of peptide is administered. If oral tolerance is desired, dosages required may be at the upper limits because of inactivation that can occur upon exposure to the digestive system.

Antigen Reactive Lymphocytes and Lymphocyte Lines

The peptides of the invention were selected to stimulate an immune response that blocks or inhibits a pathogenic immune response that results in central nervous system damage. The peptides are preferably those that block or inhibit the immune response to autoantigens such as CNP and other CNS components. While not meant to limit the invention, it is believed that one way to block or inhibit a pathogenic immune response is by the development of tolerance to the antigen. One mechanism for achieving this is by generating suppressor cells that prevent reactivity to autoantigens such as CNP.

Lymphocytes can be generated that are reactive with CNP, HSP65 and/or peptides derived therefrom. Such cells can either enhance autoimmune central nervous system disease, vaccinate against autoimmune central nervous system disease, or modulate the induction, amplification, or suppression of autoimmune central nervous system disease. The T-cells can be identified by their characteristics such as cytokine secretion profile, cell surface antigens, and T-cell receptor type. Specific T-cell populations can be selected, sorted, and amplified for use diagnostically or therapeutically.

A major use for antigen-reactive lymphocytes specific for CNP, HSP65, or peptides thereof includes a screening assay for identifying peptides or peptide analogs that block immune responses to autoantigens such as CNP. This assay can also be used to determine the amounts of peptide or peptides that will inhibit or block the immune response to an antigen such as CNP. Peptides and/or peptide analogs can be screened for their ability to block reactivity of T lymphocytes to an autoantigen such as CNP using a lymphocyte proliferation assay. Lymphocytes obtained from an animal immunized with a peptide or peptide analog can be harvested and tested for proliferation in the presence of autoantigens such as CNP or peptides derived from CNP and other central nervous system autoantigens.

A screening assay is also useful to identify peptides derived from HSP65 and that stimulate a greater response in T cells from patients with autoimmune central nervous system disease than controls. Lymphocytes can be collected from cerebrospinal fluid (CSF) and peripheral blood. Short term cell lines are generated using mycobacterial HSP65 to stimulate cells. Cells are fed with medium containing interleukin 2 and restimulated with HSP65 every 12–14 days. Cultures are harvested after 2 weeks of culture. The cells are then incubated with 5–50 $\mu$g of the peptides and the proliferative response measured using a standard assay. Proliferative responses greater than two fold above background are considered significant. Peptides that stimulate a greater response in patients with autoimmune central nervous system disease compared to control are selected.

The lymphocyte proliferation assay can also be used to determine the blocking abilities of peptides. It is a standard assay. Briefly, about $5 \times 10^4$ lymphocytes are cultured in vitro for about 3–6 days in the presence of about 5–10 $\mu$g/ml of at least one stimulating antigen. The ability of peptides to block the proliferative responses of lymphocytes sensitized to peptides derived from CNP, HSP65, or peptide analogs thereof can be determined. An inhibition of a proliferative response of about 30% to 100% is indicative that the test antigen or peptide inhibits the immune response to the stimulating antigen, and that the peptide or peptides would be selected for therapeutic use or to develop antibody reagents.

The lymphocyte proliferation assay as described above can also be used to monitor the efficacy of therapy with peptides to block or inhibit a pathogenic immune response in autoimmune central nervous system disease. Splenic or draining lymph node lymphocytes from animals immunized with at least one peptide according to the invention can be evaluated for responsiveness in vitro to autoantigens such as CNP, peptides derived from CNP, myelin basic protein, proteolipid protein, mycobacterial HSP65, or peptides derived from HSP65 during the course of treatment. Inhibition of proliferation compared to control lymphocytes of about 30% to 100% indicates that a blocking immune response has been established and/or maintained. A change in that inhibition to about 0 to 30% indicates that the animal no longer has a blocking immune response and also indicates that additional treatment with the peptides may be necessary to establish or maintain the state of unresponsiveness. It is especially preferred that the peptide block or inhibit immune responsiveness to autoantigens such as CNP or other CNS components.

It is known to those of skill in the art that lymphocytes tolerized to myelin basic protein components can transfer the tolerance to another syngeneic animal. Lymphocytes, preferably T-cell lymphocytes formed in response to a tolerizing dose of the peptides of the invention, can be identified and characterized by the profile of cytokine secretion, lymphocyte markers, and T-cell receptor type. Reagents and method of T-cell characterization are known to those of skill in the art. Once these cells are characterized, other inhibitory agents directed to these specific cell types can be prepared, including, for example, antibodies to the specific T-cell receptor type that binds to the peptide.

Once the cells are identified, those cells identified as suppressor cells can be optically sorted using FACS analyses and then amplified in vitro with T-cell growth factors. Suppressor cells can be selectively amplified by methods known to those skilled in the art. Once identified and amplified, the suppressor cells can be administered to the animal from which they were initially obtained to prevent, ameliorate, or treat symptoms of autoimmune central nervous system disease. A dosage of suppressor cells of about $1 \times 10^5$ to $1 \times 10^7$ cells would be sufficient to block a pathogenic immune response.

Lymphocytes can also be modified and used to treat and/or prevent symptoms of autoimmune central nervous system disease. Lymphocytes can be coupled to the tolerizing peptide by chemical means. T-cells can then be inactivated whether coupled with antigen or not and administered to an animal to treat, ameliorate, or prevent symptoms of autoimmune central nervous system disease. T-cells with or without the peptide are administered at a concentration of about $1 \times 10^5$ to $1 \times 10^7$ cells.

It is believed that one mechanism for blocking or inhibiting a pathogenic immune response is that T-cells specific for peptides of the invention can induce a regulatory anti-T-cell receptor response that can inhibit the pathogenic immune response. It is also believed that the peptide coupled to the T-cells can induce immune tolerance of the peptide.

Methods for Immunizing an Animal with a Peptide

The invention also includes methods for immunizing an animal with at least one peptide or peptide analog. It is preferred that the immunization with the peptide results in modulating an immune response that blocks or inhibits a pathogenic autoimmune response to central nervous system components. Inducing tolerance to at least one peptide of the invention is one way to form an immune response that can block or inhibit a pathogenic autoimmune response. Tolerization of an animal to a peptide can be useful to form a T lymphocyte population that can be used diagnostically or therapeutically as described previously. Inducing tolerance to a peptide can also be useful to treat, prevent, or ameliorate the symptoms of an autoimmune central nervous system disease such as multiple sclerosis.

The method involves administering a pharmaceutical composition to an animal in an amount effective to immunize the animal to at least one peptide and preferably tolerize the animal to the peptide. The pharmaceutical composition can include peptides derived from CNP or HSP65 or peptide analogs of both. When the pharmaceutical composition includes peptides derived from HSP65 these peptides may but do not have to share homology or cross-react with CNP. As described previously, a first class of peptides includes peptides derived from HSP65 and that share homology or cross-react with a myelin component such as CNP. A second class of peptides includes peptides derived from HSP65 that stimulate a specific T cell response in MS patients but need not share any homology with CNP.

If tolerance is desired, it is preferred that the composition is administered subcutaneously, orally, intramuscularly or intranasally. Oral administration is especially preferred. For low dose tolerance, a dose range of about 1 ng to 100 mg/kg of body weight of peptide is administered. For high dose tolerance, a dosage of about 5 ng to 100 mg/kg, preferably 20 ng to 20 mg/kg, is administered. The composition can be administered as a single dose or in multiple doses as is necessary to establish and/or maintain tolerance.

Tolerance to a peptide or peptides can be determined by examining the reactivity of peripheral blood lymphocytes in a lymphocyte proliferation assay as described previously. Splenic or draining lymph node lymphocytes from an animal immunized with at least one peptide can be obtained and cultured in vitro. The cells are then stimulated with an antigen-containing material such as the peptide used for immunization, human CNP, other myelin protein components or mycobacterial HSP65. The inhibition of proliferation of about 30% to 100% is indicative of a state of tolerance.

The maintenance of tolerance to the peptide can be evaluated over time and if lymphocyte proliferative responses change, the composition can be re-administered until tolerance to the peptide is again established and/or maintained.

In a preferred version, the composition is administered to a patient who has the symptoms of an autoimmune central nervous system disease such as multiple sclerosis. A pharmaceutical composition including at least one peptide is administered to the patient in a dose effective to block or inhibit a pathogenic immune response and/or to establish tolerance to the peptide. The pharmaceutical composition preferably includes at least one peptide that protects against the development of EAE such as (CNP peptide 176 to 184) leu-lys-pro-gly-leu-glu-lys-asp-phe (SEQ ID NO:1) coupled to KLH, (HSP peptide #6) lys-gly-tyr-ile-ser-gly-tyr-phe-val-thr-asp-ala-glu-arg-glu (SEQ ID NO:11) (HSP peptide #8) gly-gly-val-thr-leu-leu-gln-ala-ala-pro-ala-leu-asp (SEQ ID NO:13) or (HSP peptide #9) val-ala-val-lys-ala-pro-gly-phe-gly-asp-arg-arg-lys-ala-met (SEQ ID NO:18). The pharmaceutical composition is administered orally, subcutaneously, intramuscularly, intranasally or intravenously at sufficient intervals and dosages to establish tolerance.

Methods of Treating or Preventing Autoimmune Disease of a Central Nervous System The invention also includes methods of preventing, ameliorating, or treating autoimmune inflammatory disease of the central nervous system Central nervous system diseases that are known to involve autoimmune responses include multiple sclerosis, Behcet's Syndrome, acute disseminated encephalomyelitis, Whipple's disease, cranial arteritis, primary brain tumors, and post vaccinal encephalomyelitis. A method involves administering a pharmaceutical composition including at least one peptide of the invention in an amount effective to prevent, ameliorate, or treat symptoms of the disease.

The pharmaceutical composition includes those peptides that, upon immunization or administration, provide for an immune response that blocks or inhibits a pathogenic response to autoantigens of the central nervous system. Preferably, the peptides are administered in an amount to tolerize the patient to self-antigens such as those found on CNP and other CNS components.

While not meant to limit the invention, it is believed that down regulation of responsiveness to self-antigens such as CNP can be accomplished by inducing anergy, tolerance or suppressor T lymphocyte responses to the peptides of the invention. In addition, peptides may compete for binding to MHC and T cell receptor molecules and thereby prevent formation of an autoimmune response or they may induce secretion of anti-inflammatory cytokines.

Optionally, the peptides of the invention can be further selected based upon the major histocompatibility antigens-class II (MHC) genotype of the patient to be treated. Patients with different MHC genotypes may have different patterns of response to the peptides of invention. For example, for male patients having the DR2 genotype, peptide 5 derived from HSP65 is preferred. Patient lymphocyte reactivity to the peptides of the invention can be determined by screening patients lymphocytes as described in Example 7.

Efficacy can be monitored by a decrease in severity or presence of symptoms such as weakness, loss of balance or vision, tremors, sensory changes, or bowel and bladder incontinence using standard methods. Changes in spinal fluid and on brain imaging can also be utilized. Changes in brain images include CT scans, MRI scans, SPECT scans, PET imaging, and MR spectroscopy and can be identified using standard methodology.

The pharmaceutical composition can be administered intravenously, orally, subcutaneously, or intramuscularly. The composition may be administered in a single dose or in multiple doses. The amount administered is that amount effective to decrease symptoms of the disease as described above. The amount is preferably that amount that blocks or inhibits the pathogenic immune response to an autoantigen. This amount can be determined using a lymphocyte proliferation assay. This amount is preferably a tolerizing does as described previously.

The composition is administered to a patient who has symptoms or has been diagnosed with autoimmune central nervous system disease. The composition is preferably administered immediately after diagnosis, during acute exacerbations, or during the chronic phase of the disease. The composition may be especially useful for treating patients experiencing acute exacerbations of the disease to decrease severity of symptoms and prevent further damage. A decrease in severity or presence of symptoms is evaluated weeks to months after administration of the pharmaceutical composition.

All publications are herein incorporated by reference to the same extent as if each individual publication was specifically and individually indicated by reference.

It will be appreciated by one of ordinary skill in the art that many changes and modifications can be made in the invention without departing from the spirit or scope of the appended claims.

EXAMPLE 1

Binding of Antibodies to Myelinated Cells

Tissue sections from normal adult human spinal cord, from areas of the brain lacking myelin and myelinated peripheral nerves were stained with murine monoclonal antibodies specific for epitopes on the 65 kD heat shock protein from *Mycobacterium leprae*. The results are shown in FIGS. 1a, b and c.

Murine monoclonal antibodies to mycobacterial antigens were obtained from the UNDP/World Bank/WHO Special Program for Research and Training in Tropical Disease Repository at the Center for Infectious Diseases, Centers for Disease Control, Atlanta, Ga. Antibody 11H9 (mc5205CDC/WHO reference number) and IIC8. (mc4220) were obtained from the depository. Antibody 11H9 is known to recognize amino acids 115 to 123 of *Mycobacterium leprae* HSP65 protein. Antibody IIC8 is specific for a different epitope on mycobacterial HSP65. Antibodies to bovine cyclic nucleotide phosphodiesterase (CNP) designated R423/13 were prepared as described in Example 2.

Sections of normal human spinal cord obtained at autopsy, were cut into 1×1×0.5 cm pieces, then fixed in 10% buffered formalin for 1.5–2 hours. Tissues were then immersed in 7% sucrose solution at 4° C. overnight followed by incubation in 15% sucrose solution at 4° C. for 2–6 days. After embedding and freezing tissues in Tissue-Tek embedding medium (O.C.T. compound), Miles, Inc., Diagnostic Division, Elkhart, Ind., 10μ thick frozen sections were placed on gelatin coated slides, washed with phosphate buffered saline, then incubated with primary and secondary antibodies using the technique described in the Vectastain Elite ABC Kit (Vector Laboratories, Burlingame, Calif.). Primary antibodies were used at dilutions of 1:1–2,000 Antibody binding to tissues was detected with the avidin-biotin, immunoperoxidase technique recommended in the Vectastain Kit. Sections from human brain and peripheral nerves were prepared and stained in the same manner.

Figure 1C:
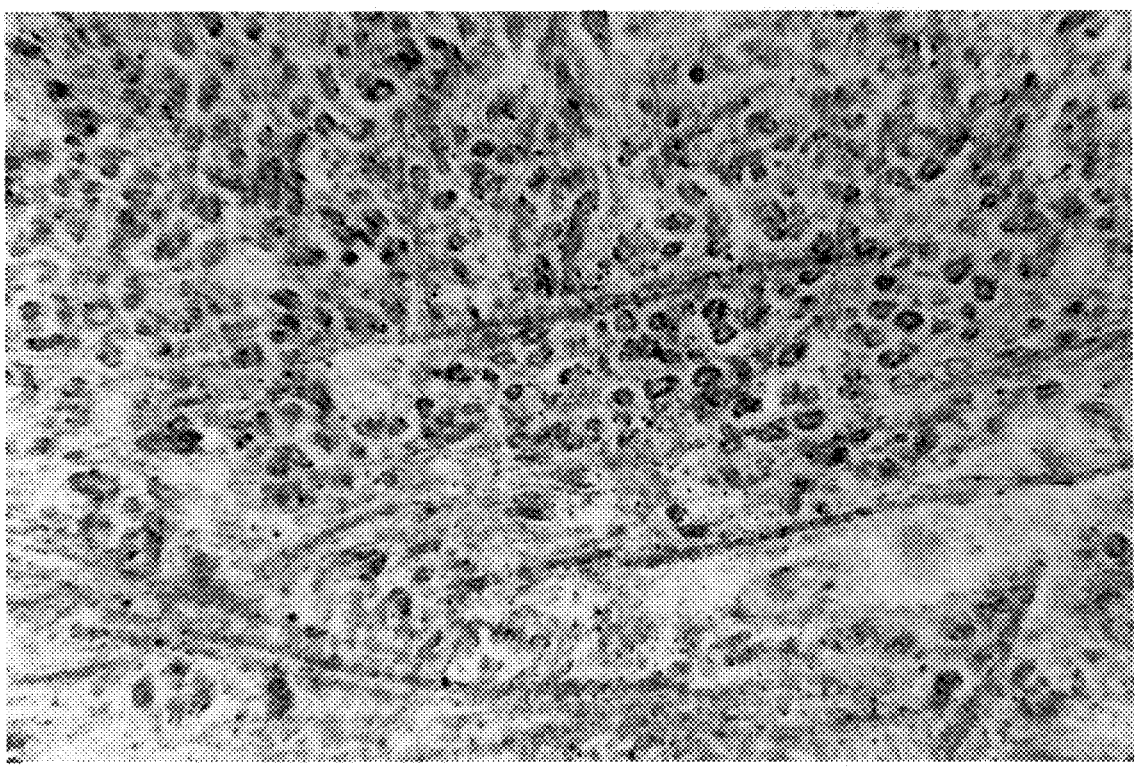

Staining patterns differed, especially in regard to staining of myelin. Results with two antibodies are shown in FIGS. 1a and b. Antibody IIH9, specific for amino acids 115–123 of *M. leprae* HSP65, stained myelinated fibers with no staining of neurons or glia. In contrast, IIC8 stained neurons and axons but not myelin. FIG. 1c shows staining of normal human spinal cord with a polyvalent rabbit anti-CNP antibody (R423/13). Staining of myelin by anti-CNP antibody is equivalent to that seen with antibody IIH9. When sections were prepared from areas of brain lacking myelin, such as at the edges of demyelinated plaques in brains from persons with MS, binding of IIH9 was not seen (data not shown). Staining of myelinated peripheral nerves was noted with IIH9 but not IIC8 (data not shown).

These results indicate that antibodies specific for mycobacterial HSP65 and CNP recognize a component of myelinated cells.

EXAMPLE 2

Binding of Antibodies to Components of Myelin

Immunoblots were used to determine which myelin proteins were involved in the binding of antibodies to myelinated tissues as described in Example 1. Immunoblots were performed on proteins of sucrose gradient-purified, delipidated human, rat and bovine myelin. The method of myelin isolation was that described by Norton et al., *J. Neurochem.*, 21:749–757 (1973).

A panel of monoclonal antibodies to human and mycobacterial hsp and to some lower molecular weight mycobacterial proteins were tested.

Antibodies: Murine monoclonal antibodies to mycobacterial hsp were from the UNDP/World Bank/WHO Special Programme for Research and Training in Tropical Diseases repository at the Center for Infectious Diseases, Center for Disease Control, Atlanta, Ga. Numbers of these antibodies are the suppliers' designation with CDC/WHO reference numbers in parentheses: IIH9 (mc5205), IVD8 (mc2404), ML04-$A_2$ (mc3607), ML06-$A_2$ (mc8908), L5 (mc8026), F47-9 (mc5828), $SA_1D_2D$ (mc5041), L7 (mc0044), ML30-$A_1$ (mc2009), IIIC8 (mc4243), IIIE9 (mc9215), IIC8 (mc4220), WTB78 (IT-13), and HAT 3 (IT-41). Murine monoclonal antibody to human HSP60 (II-13), was generously donated by Dr. Radhey S. Gupta, McMaster University, Hamilton, Ontario, Canada. Rabbit polyclonal antibody, $P_2II$, to Chinese Hamster HSC70 was also supplied by Dr. Gupta. Murine monoclonal N27F3-4 recognizes the constitutive (73 kD) and inducible (72 kD) forms of human HSP70. C92 recognizes only the inducible 72 kD form. Both were kindly supplied by Dr. William J. Welch, University of California, San Francisco. Rabbit polyclonal antiserum R423/13 to bovine CNP was prepared in our own laboratories using standard methods (Dr. Peter E. Braun, McGill University).

Immunoblotting: The basic SDS-PAGE technique of Laemmli, as modified by Blomster-Hautamaa was used (*J. Immunol.*, 137:3572 (1986)). Proteins were separated on either 10% or 13% polyacrylamide gels. Proteins were electrophoretically transferred to nitrocellulose, pore size 0.22μ. Non-specific binding sites on the nitrocellulose were blocked with 3% gelatin in Tris buffered saline (TBS). Primary antibodies were diluted in TBS containing 0.05% polyoxyethylene sorbitan monolaurate (Tween 20) (Sigma Chemical Co., St. Louis, Mo.). Antibodies were incubated with the nitrocellulose strips at 4° C. overnight. Secondary antibodies, consisting of alkaline phosphatase conjugated goat anti-murine polyvalent Ig or goat anti-rabbit IgG antibodies (Sigma Chemical Co., St. Louis, Mo.) were incubated with the nitrocellulose for 2 hours at 37° C. After washing, strips were incubated with substrate, consisting of 5-bromo-4-chloro-3-indolyl phosphate (BCIP) (Sigma #B8503); Nitroblue Tetrazolium (NBT) Sigma #N6876); N,N-Dimethylformamide (Sigma #D4254) and 2M $MgCl_2$ 4 mg BCIP was dissolved in 0.8 ml dimethylformamide. 8 mg NBT was dissolved in 4.0 ml water. The dissolved BCIP and NBT were added to 36 ml barbitol buffer (0.15M, pH9.6) with 80 ul of 1M $MgCl_2$. Since intensities of the bands were related to time of incubation in substrate, all strips with the same species of primary antibody were developed for the same period of time.

Figure 2:
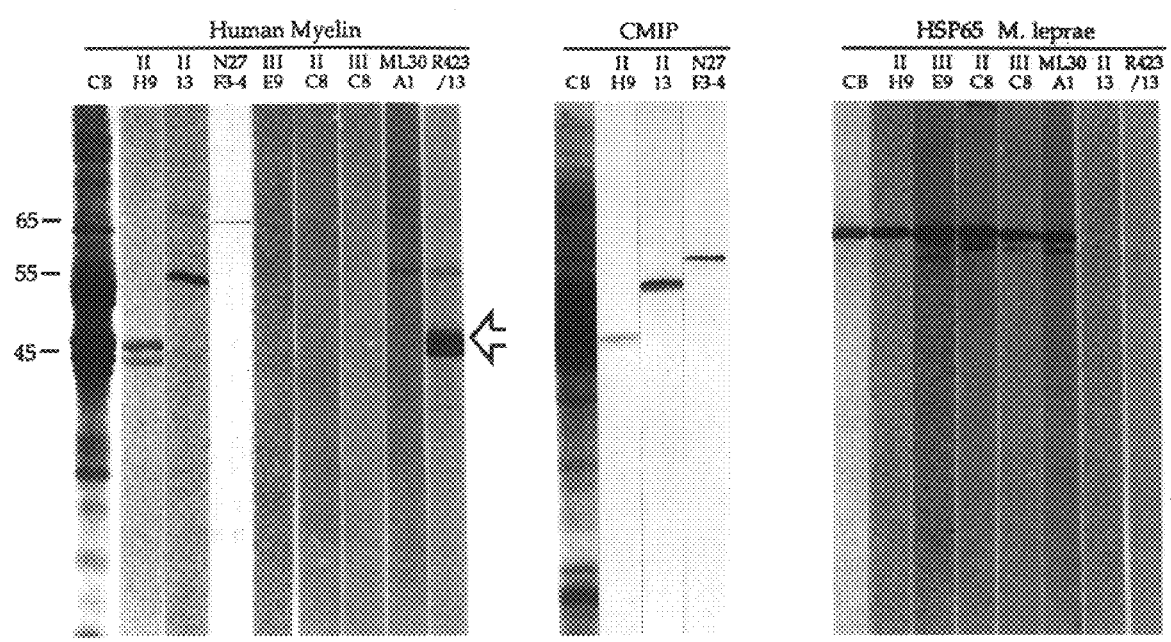
FIG. 2: Immunoblots of whole myelin and CMIP (chloroform-methanol insoluble pellet), and HSP65 labeled with antibodies to HSP and CNP. CB indicates lanes of proteins stained with Coomassie blue. Antibodies II H9, II 13, N27F3-4, III E9, II C8, III C8, MC30AI are specific for heat shock proteins and are described in Example 2. Antibody R423/13 is specific for cyclic nucleotide phosphodiesterase (CNP) as described in Example 2. The arrow points to the two isoforms of CNP identified by the polyvalent anti-CNP antibody, R423/13.

The results are shown in FIG. 2. Only 3 of the 17 monoclonal antibodies to hsp bound to polypeptide components of myelin. Those monoclonal antibodies are: 1) IIH9 specific for mycobacterial HSP65; 2) II-13 specific for human HSP60; and 3) N27F3-4 specific for human HSP72/73. Reactive polypeptides differed with the different monoclonals, ranging in size from ~46 kD to ~65 kD (FIG. 2). No binding occurred in regions corresponding to myelin basic protein (MBP) or proteolipid protein (PLP), the two major myelin proteins.

When myelin was extracted with chloroformmethanol, a procedure that reduces the amounts of MBP and PLP, binding of the monoclonals to the residual polypeptides (CMIP) was unaffected (FIG. 2). One of the monoclonals, IIH9, bound to a doublet of MW 46 and 48 kD. This doublet corresponded in mass to CNP in both immunoblots and Coomassie blue stained acrylamide gels. Since the two isoforms of CNP (CNP1 at ~46 kD, and CNP2 at ~48 kD) arise by alternative splicing of a primary gene transcript differing only by 20 amino acids at the N-terminus, an immunoreactive doublet is expected if the epitope is not in the first 20 residues of CNP2. To pursue this further, immunoblots using recombinant CNP as antigen were prepared.

These results indicated that an antibody specific for mycobacterial HSP65 recognized and bound to a component of myelin having a molecular weight of 46–48 kD.

EXAMPLE 3

Binding of Monoclonal Antibodies Specific for Mycobacterial HSP65 to Cyclic Nucleotide Phosphodiesterase Once a doublet component with a molecular weight 46 and 48 kD was identified by staining with a monoclonal antibody to HSP65, reactivity with antibodies to bovine CNP (R423/13) was evaluated. This component was analyzed further for identity of any shared sequence homology.

Antigens: Recombinant rat CNP (isoform 1) was expressed in Sf9 cells using the baculovirus expression vector system. Most of the expressed CNP1 remained avidly associated with cellular components by virtue of its isoprenylated C-terminus (Cox et al, *J. Neurosci.*, 39:513–518 (1994)). Whole cell lysates were used in immunoblots.

A 12-residue antigenic peptide, corresponding to amino acids 173 to 184 of CNP isoform 2 (Leu-Lys-Lys-Leu-Lys-Pro-Gly-Leu-Glu-Lys-Asp-Phe) (SEQ ID NO:17) was synthesized using the Fmoc commercial chemical procedure. A cysteine was added at the C-terminus for ease of coupling to albumin. This coupling was carried out with the Imjet Activated Immunogen Conjugation Kit (Pierce Chemical Co., Rockford, Ill.). The carrier used was maleimide-activated bovine serum albumin. Since this protein contained ~25 moles of maleimide per mole of protein, the synthetic peptide generated products of varying sizes in the range of 95 kD due to non-specific aggregation.

Recombinant HSP65 from *M. leprae* (Batch ML65-5b), was a gift from Dr. J. D. A. van Embden; Head, Unit Molecular Microbiology; Rijkinstituut Voor Volksgezondheid en Milieuhygiene, Bilthoven, The Netherlands.

These antigens were tested for reactivity with the antibodies as described in Example 2. The results are shown in FIG. 3.

Figure 3:
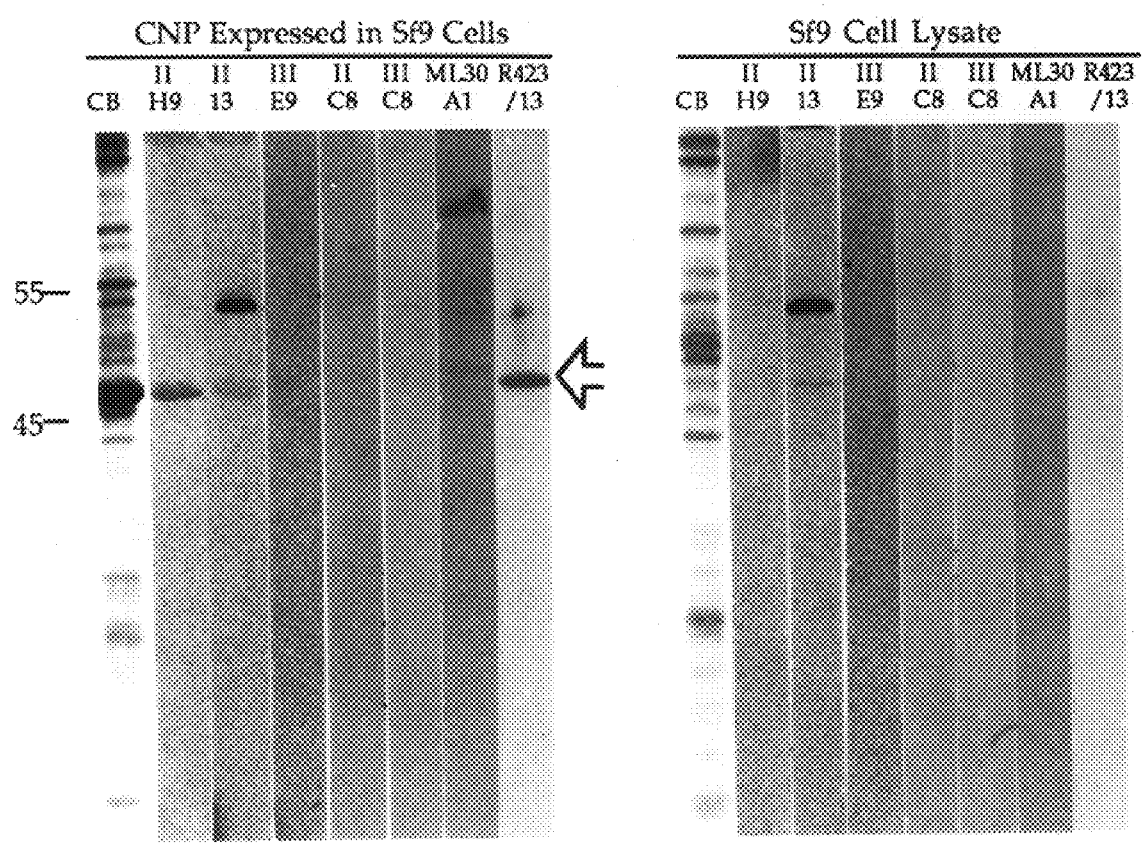
FIG. 3: Immunoblots showing labeling of CNP produced in Sf9 cells. The arrow points to the CNP1 isoform of CNP.

Antibody IIH9 bound to recombinant CNP1 in a pattern identical to that noted with rabbit anti-CNP antibody (FIG. 3). Monoclonals ML30-$A_1$, IIC8, IIIE9, IIIC8, all reactive with mycobacterial HSP65, did not bind to CNP (FIG. 3).

A search for primary structure similarities between CNP and the 20-residue HSP65 peptide that contains the epitope recognized by IIH9 was conducted using the FASTA program. A visual analysis confirmed that the two proteins share a 9-residue peptide in which 7 amino acids are either identical or closely related (FIG. 4). The nine residue peptide of CNP corresponds to amino acids 176 to 184 of CNP isoform 2 and has the following sequence: Leu-Lys-Pro-Gly-Leu-Glu-Lys-Asp-Phe (SEQ ID NO:1). This region of CNP is completely conserved in all species examined (mouse, rat, cow, human) (Gravel et al., *J. Neuro. Sci. Res.*, 38:243 (1994)).

Figure 5:
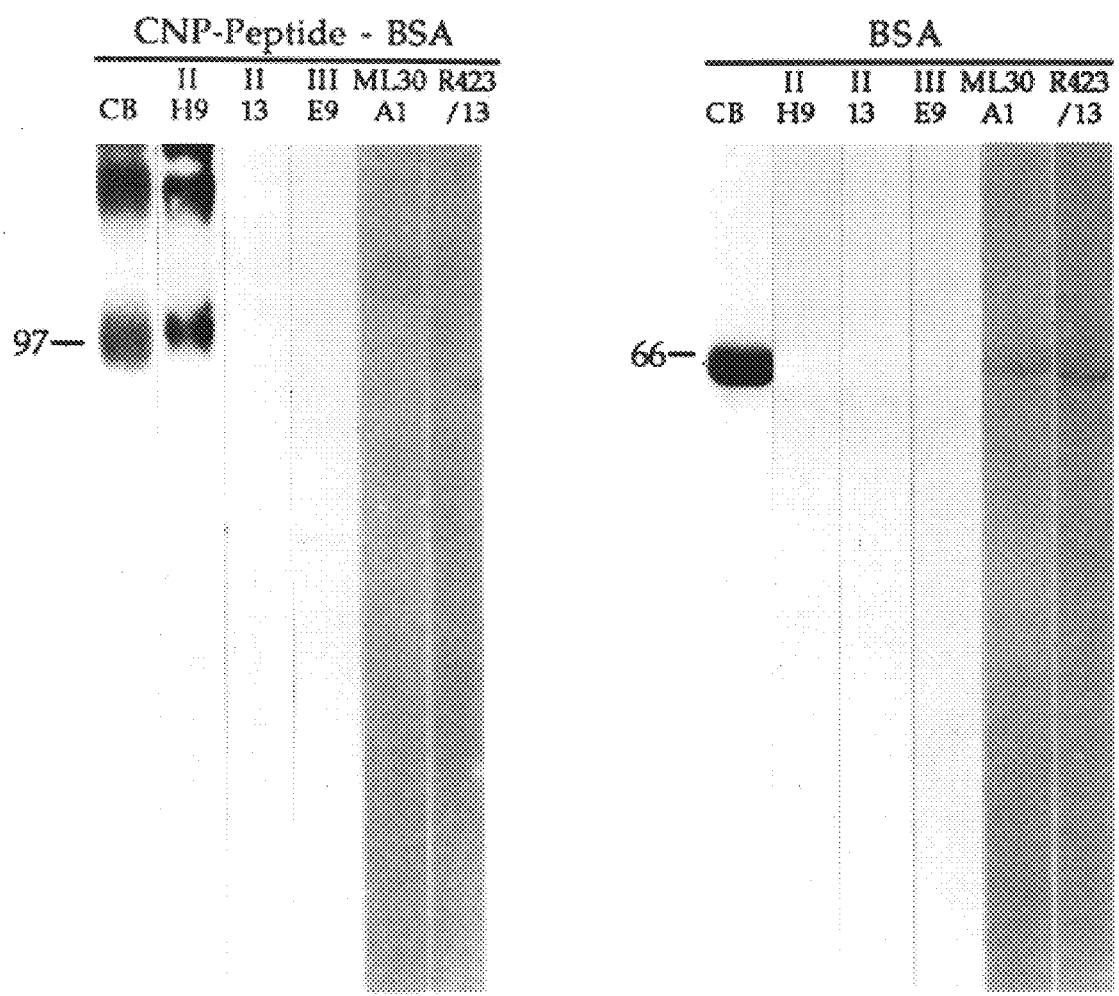
FIG. 5: Immunoblots showing labeling of CNP 173–184 peptide coupled to BSA.

A 12-amino acid peptide from CNP encompassing this region of homology was coupled to bovine serum albumin as described previously, and tested for its reactivity with IIH9. Results are shown in FIG. 5. Antibody IIH9 bound strongly to the peptide-coupled albumin but not to albumin alone. None of the other antibodies showed similar binding.

This is the first demonstration of immunologic cross-reactivity between a heat shock protein and a protein of CNS myelin, CNP. CNP has long been an enigma since no cellular or physiological function can be attributed to its ability to catalyze hydrolysis of the 2', 3'-cyclic nucleotides (Sprinkle, T. J., *Crit. Rev. Neurobiol.*, 4:235 (1989)). Although CNP is unique to oligodendrocytes in the CNS, and to Schwann cells in the peripheral nervous system, several other cell types express it less abundantly such as lymphoid tissues and some photoreceptor cells. As the earliest of all known myelination-related proteins to appear developmentally in oligodendrocytes, CNP is concentrated mostly near the plasma membrane of these cells (Braun et al., *Ann. NY Acad. Sci.*, 608:58 (1990)).

EXAMPLE 4

Effect of Immunization with a Peptide Derived from CNP on Experimental Allergic Encephalomyelitis (EAE)

The effect of immunization with the 12 amino acid peptide corresponding to amino acids 173–184 of CNP on experimental allergic encephalomyelitis was examined.

Induction and modulation of experimental autoimmune encephalomyelitis (EAE): Young (100–125 grams), female Lewis rats were immunized subcutaneously with 0.1 cc of emulsion containing 1 mg of lyophilized guinea pig spinal cord (GPSC) in complete Freund's adjuvant (CFA), supplemented with killed H37ra strain of *M. tuberculosis* (Difco Labs., Detroit, Mich.), at 5 mg per ml of adjuvant. With this protocol, almost all animals develop an acute, monophasic illness, approximately 8–10 days after immunization. Severity of disease was graded on a scale of 1 to 5 (1=flaccid tail. 5=death) with intervals of 0.5. Half values were given if paresis rather than plegia was present.

To modulate EAE, rats were injected subcutaneously either with 50 μg of the CNP 173–184 peptide (HSP-CNP peptide) coupled to keyhole limpet hemocyanin (KLH) or 50 μg of KLH alone. Proteins were emulsified either in incomplete Freund's adjuvant (IFA) or Complete Freund's Adjuvant (CFA) supplemented with 5 mg/ml MTb.H37a(SCFA). Five to six weeks later all animals were immunized with GPSC in CFA, as described above. Clinical examinations of animals were performed by the same individual in all experiments. Differences in the means between the two groups were calculated using Student's t-test, assuming a two-tailed distribution with equal variances.

None of the Lewis rats immunized with the CNP 173–184 peptide coupled to keyhole limpet hemocyanin (KLH) or control rats immunized with KLH developed EAE. Five to six weeks after primary immunization, all groups received GPSC emulsified in CFA.

Figure 6:
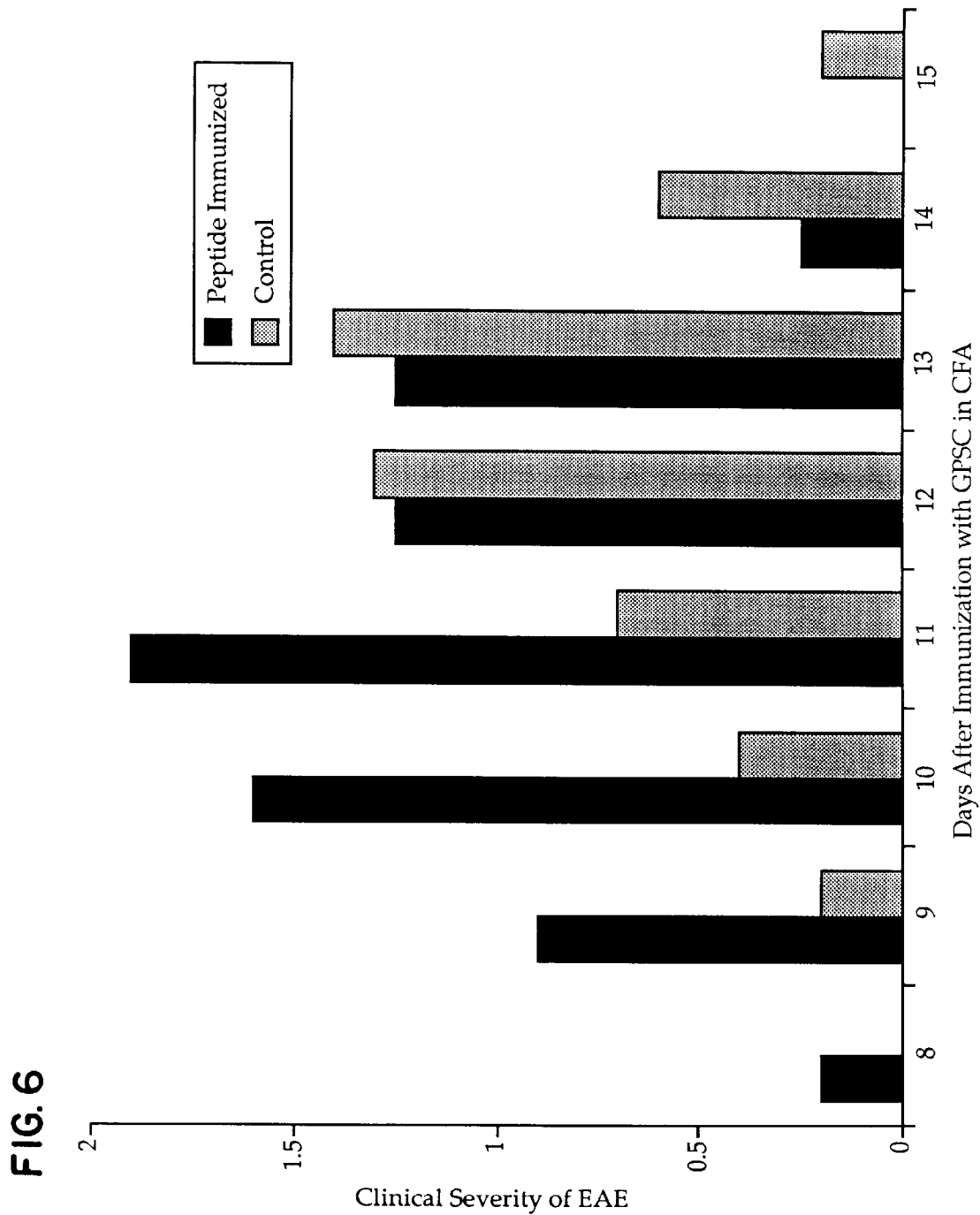
FIG. 6: Pre-immunization of rats with CNP 173–184 peptide coupled to KLH in Complete Freund's Adjuvant (CFA) results in enhanced Experimental Autoimmune Encephalitis (EAE). The bars indicate the arithmetic means of disease severity scores from groups of 5–6 rats.

The results are shown in FIG. 6. Rats pre-immunized with CNP 173–184 peptide-KLH in CFA developed EAE that was more severe and peaked earlier than did rats pre-immunized with KLH in CFA (FIG. 6). Differences in the means between the two groups on Day 10 following spinal cord immunization were statistically significant (p<0.05).

Figure 7:
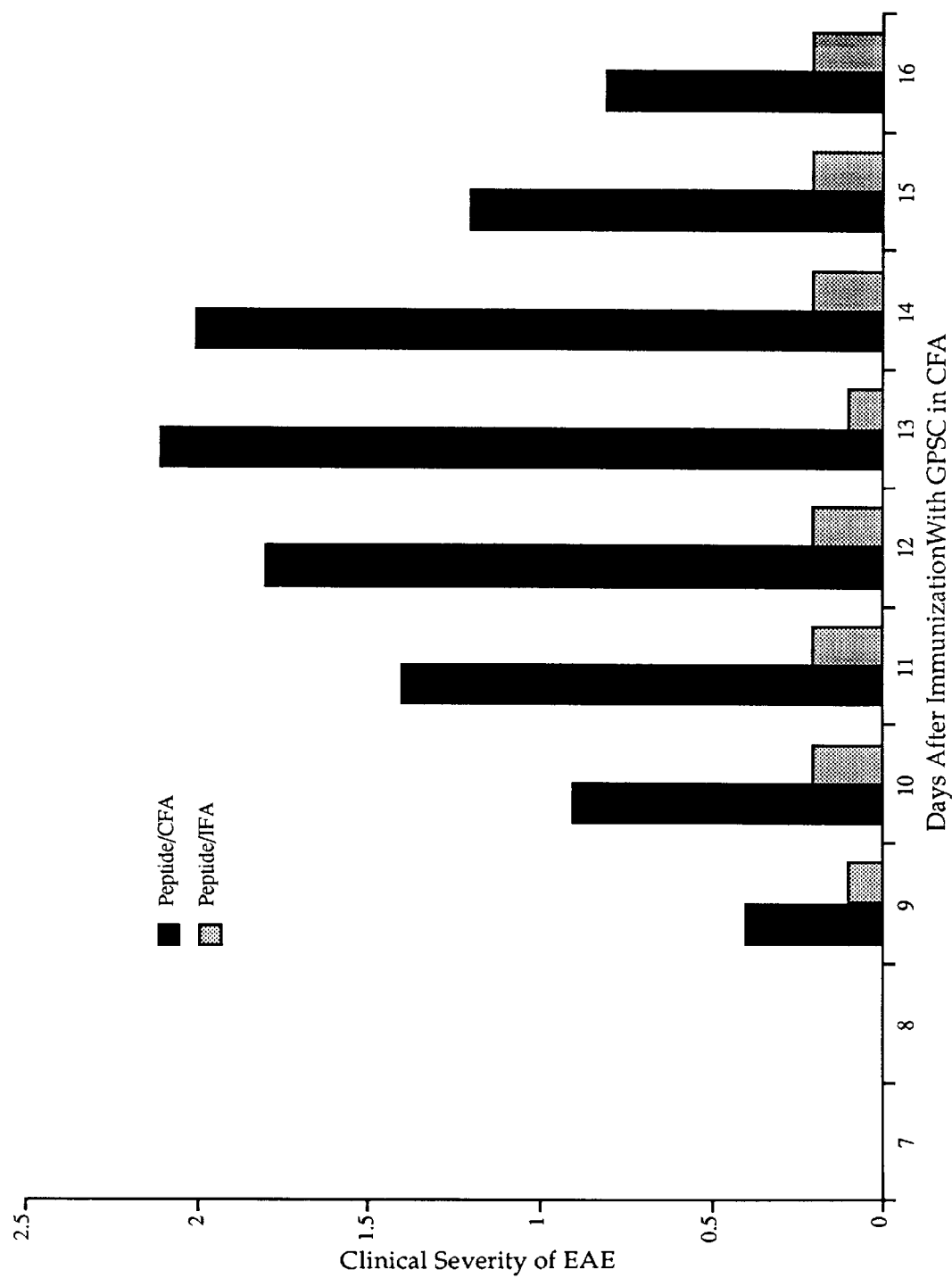
FIG. 7: Pre-immunization with CNP 173–184 peptide coupled to KLH in Incomplete Freund's Adjuvant (IFA) protects rats against EAE. The bars indicate the arithmetic means of disease severity scores from groups of 5–6 rats.

In contrast, animals immunized with CNP 173–184 peptide-KLH in IFA either failed to develop EAE when subsequently challenged with guinea pig spinal cord in CFA (40%), or developed very mild disease. Results are shown in FIG. 7. Differences between peptide-CFA and peptide-IFA pre-immunized animals were significant on Day 13 post GPSC challenge (P<0.03).

Figure 8:
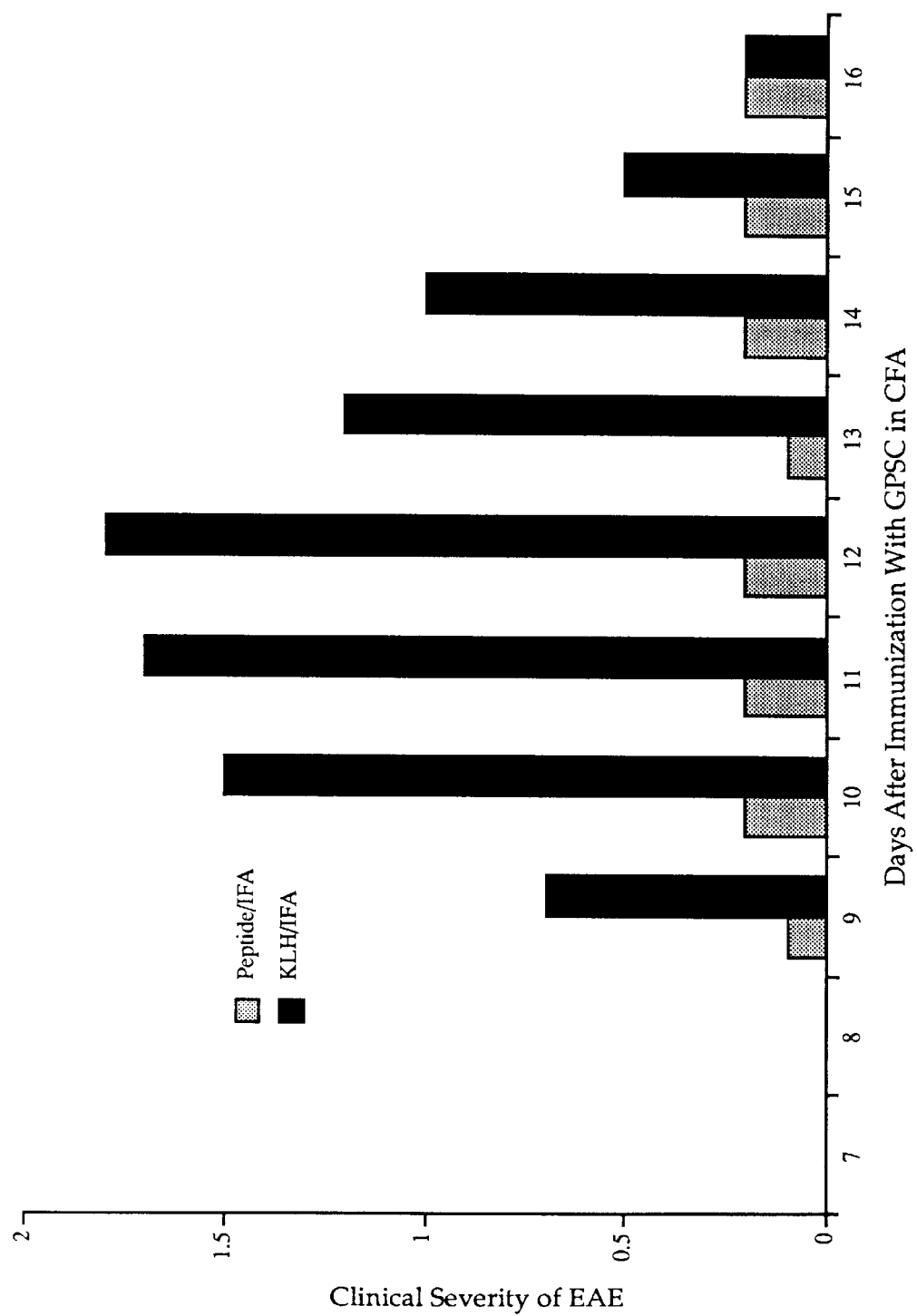
FIG. 8: The protective effect of pre-immunization with CNP 173–184 peptide coupled to KLH in IFA is antigen specific. The bars indicate the arithmetic means of disease severity scores from groups of 5–6 rats.

Animals pre-immunized with KLH and IFA and then immunized with GPSC developed severe EAE. A comparison of EAE severity in peptide-IFA and KLH-IFA pre-immunized rats is shown in FIG. 8. Differences between the two groups on day 13 post GPSC-CFA immunization are significant (p<0.02). Thus, suppression of EAE was the result of an antigen specific immune response to CNP 173–184 peptide.

EAE in rats immunized with KLH in IFA was more severe than in rats immunized with KLH and CFA (data not shown). This indicates that the phenomenon of increased severity of EAE in peptide-CFA pre-immunized animals is particularly robust, since it occurred in the face of a protective effect seen when CFA is used to preimmunize animals.

The data indicate that immunologic cross-reactivity between hsp and CNP has significant biologic consequences. They establish that a peptide of CNP can function as an autoantigen and that an immune response to this autoantigen can alter the course of EAE induced by a complex of unrelated encephalotigenic myelin proteins present in guinea pig spinal cord (e.g. myelin basic protein and proteolipid protein). It is unlikely that this phenomenon results from a non-specific immunosuppressant effect of the CNP peptide.

While not meant to limit the invention, it is believed that an immune response to this cross-reactive peptide serves as a final common pathway for the development of this autoimmune disease.

EXAMPLE 5

Detection of Anti-CNP Immune Responses in Patients with Multiple Sclerosis

It was previously shown that lymphocytes from spinal fluids of persons with MS respond to mycobacterial antigens. (Birnbaum, et al, Annals of Neurol., 1993). In addition, we demonstrated that antibodies to hsp and mycobacterial proteins are present in the spinal fluids (CSF) of persons with MS (Neurology, 1992 & 1993).

Cerebrospinal fluid (CSF) and sera from MS patients and controls were analyzed for antibodies to the peptide derived from CNP isoform 2 (corresponding to amino acids 173–184) using dot-blot analyses. Samples from nine MS patients and five patients with other neurologic diseases (OND) were analyzed. The CNP 173–184 peptide coupled to BSA was adsorbed onto nitrocellulose membranes. Control wells received BSA alone. Two dilutions of paired spinal fluids and sera were added to the wells and the amount of antibody binding determined using peroxidase labeled anti-human IgG and an enhanced chemiluminescent assay (ECL Western Blotting Kit; Amersham International, Plc., Buckinghamshire, England). Using the public domain program, Image 1.40 (available from NIH), the integrated densities of the dots in the CNP 173–184 peptide wells and BSA wells were determined.

The results indicate that CSF from 5/9 MS patients and 0/5 OND patients had antibodies to CNP 173–184 peptide (data not shown). Densities in peptide wells with MS CSF were approximately twofold higher than in BSA wells. Using chi square analysis, differences between these groups were significant (p<0.03). Antibodies to CNP 173–184 were also present in sera from 3 MS patients and 1 OND patient.

These observations indicate there is an immune response to the CNP 173–184 peptide within the CNS of persons with MS. Such an immune response may contribute to the perpetuation or amplification of demyelination in MS.

EXAMPLE 6

Lymphocyte Proliferation to Peptides Derived from HSP

Patterns of immune response to hsp peptides may differ depending on the MHC genotype of an individual. Such patterns may be specific for particular diseases, as described in patients with Behcet's Syndrome (Pervin et al, J. Immunol., *ISI:* 2273; 1993). The responsiveness to some peptides may be greater in individuals having a certain MHC type.

To determine whether patients with MS showed disease specific patterns of response to peptides of hsp, eight peptides derived from the HSP65 kDa protein of *M. leprae* were tested for the ability to stimulate proliferation of lymphocytes from these patients. The sequence and amino acid members of the peptides are shown in Table 1 on page 14.

Peptides were initially selected on the basis of being delineated as human T cell epitopes (Lamb et al; 1987; Embo. J.; 6; 1245; Von Schooten, et al, 1988; Euro. J. Immunol.). Four peptides from this group were chosen on the basis of their having at least a 5 amino acid residue identity with CNP (Peptides #5 through #8). One peptide was chosen for its lack of homology with CNP (Peptide #9). Peptides that evoked strong T cell proliferative response in patients with Behcet's disease were analyzed for evidence of sequence homology to CNP. Remarkably, three of the peptides had sequences of between 6 to 8 amino acids that were identical to sequences of CNP. These three peptides (#10, 11,12) were prepared and used in the proliferation assays. The sequences of the peptides are shown in Table 1. (Lamb et al; 1987; Embo. J.; 6:1245; Von Schooten, et al, 1988; Euro. J. Immunol. and Pervin et al, J. Immunol., 151:2273; 1993). The sequence for peptide 9 corresponds to amino acids 272 to 286 of *M. leprae* HSP65: val-ala-val-lys-ala-pro-gly-phe-gly-asp-arg-arg-lys-ala-met (SEQ ID NO:18). This peptide is not homologous to CNP and serves as a control.

Peripheral blood lymphocytes (PBL) were prepared using standard gradient centrifugation techniques from 44 patients with MS, 7 persons with other neurological disease (OND), and 11 normal individuals. Of the 44 MS patients, 40 (25 females and 15 males) were HLA-DR typed, but not sub-typed. The age, sex, and HLA-DR phenotype distributions are shown in Table 2 below.

TABLE 2

| Clinical Diagnosis | Number | DR Type | Mean Age |
| --- | --- | --- | --- |
| MS - Females | 28 | 15 - DR2+ | 27 years |
| MS - Males | 16 | 7 - DR2+ | 38 years |
| OND - Females | 5 | Not Done | 56 years |
| OND - Males | 2 | Not Done | 42 years |
| Normal - Females | 8 | Not Done | 41 years |
| Normal - Males | 3 | Not Done | 26 years |

Cells were cultured in RPMI 1640, supplemented with 15% pooled human serum, antibiotics, and supplemental L-glutamine, and stimulated with delipidated, whole, normal human myelin (prepared by Dr. John Trotter of Washington University, St. Louis, Mo.), killed, sonicated, whole M. tuberculosis (Strain H37ra, Difco Labs, Detroit, Mich.), and with the eight peptides described above. Proliferative responses were measured using a thymidine incorporation assay (Birnbaum, et al., 1990; Neurol. 40:1785). To allow comparisons between experiments, results were converted to multiplicities of background proliferation. Background proliferation obtained from autologous PBL cultured without antigens. To ensure that cultures were viable and could proliferate, all experiments included PBL cultured with PHA-P. Multiplicities greater than two-fold above background were considered significant. Statistical analyses of the data were performed using Student's t-test, chi-square analyses, and Pearson's correlation coefficient test.

As described previously in Birnbaum, et al., 1993; Am. Neurol., 34:18, persons with MS responded strongly to whole, sonicated *M. tuberculosis*. No differences were noted in the frequency of proliferative response to myelin among the different groups. PBL from 29 MS patients and 7 with OND were stimulated with the eight peptides described above. All of the tested peptides elicited a response in some individuals.

Using chi-square analyses, we determined whether there were significant differences in the frequencies of responses to all of the hsp peptides among different groups of MS and OND patients. Responses to only four peptides showed significant differences. These results are presented in Table 3.

TABLE 3

Differences Between Patient Populations in Responses to HSP Peptides

| Group A greater than Group B | Peptide #5 | Peptide #6 | Peptide #9 | Peptide #12 |
| --- | --- | --- | --- | --- |
| MS F vs MS M | N.S. | p <0.025 | N.S. | N.S. |
| MS F, DR2− vs MS F, DR2+ | N.S. | N.S. | p < 0.025 | N.S |
| MS M, DR2+ VS MS F, DR2+ | p < 0.05 | N.S. | N.S. | p < 0.05 |
| MS F, DR2− VS MS M, DR2− | N.S. | p < 0.05 | N.S. | N.S. |
| MS F vs OND M | N.S. | p < 0.0005 | N.S. | N.S. |

F = females.
M = males.
N.S. = Not Significant.

These results show that MS females had a greater response to peptide 6 than MS and OND males. Non DR2 MS females responded more strongly to peptide 6 than did non-DR2 MS males. MS DR2+ males had a stronger response to peptide 5 and peptide 12 than MS DR2+ females. MS females DR2− had a stronger response to peptide 9 than the MS females carrying DR2.

The results indicate that there are differences in the responses to hsp peptides among different patient populations, and that differences may be related to gender, disease, and DR genotype. This is the first demonstration of an immune response gene effect related to hsp peptides in persons with MS.

Proliferative responses to *M. tuberculosis* and hsp peptide were correlated with each other as well as with particular DR genotypes. T-cell proliferative responses to *M. tuberculosis*, especially those in spinal fluid, are increased in persons with MS. Pearson correlation coefficients were used to determine the significance of the associations of positive responses (data not shown).

Peptide #6: There was a significant correlation (p<0.01) between responsiveness to hsp peptide #6 and responsiveness to *M. tuberculosis* in all patients with MS, both males and females. When groups were divided by sex and DR genotype, only DR2+females and DR2−males showed significant correlations (p<0.02 and <0.01 respectively). No significant correlations were noted in the OND patient group.

Peptide #7: All MS patients showed significant correlations between responsiveness to this peptide #7 and *M. tuberculosis* (p<0.01). When MS patients were further divided on the basis of sex and HLA-DR genotype, DR2+ females were the predominant responders among MS females (p<0.01). No MHC predilection was noted in male MS patients. No significant correlations were noted in patients with OND.

Peptide #8: There was a significant correlation (p<0.05) between responsiveness to hsp peptide #8 and responsiveness to M. tuberculosis in all MS patients analyzed as a group. When MS patients were further divided as described above (male, female, DR2+, DR2–), only female DR2+ MS patients showed a significant correlation (p<0.05). No significant correlations were noted in patients with OND.

Peptide #9 (No CNP Homology): There was a statistically significant negative correlation (p<0.05) between proliferation to peptide #9 and responsiveness to M. tuberculosis in DR2– MS females. All other MS patient categories failed to show any associations. In contrast to the above peptides, OND females demonstrated a significant correlation (p<0.05) between responsiveness to Peptide #9 and M. tuberculosis.

Peptides #10 & 11: Only male MS patients showed significant correlations (p<0.01) between responses to peptides #10 and #11 and responses to M. tuberculosis. For Peptide #11, the correlation was further limited to DR2– males with MS.

Peptide #12: No significant correlations were found in peptide #12 for any of the MS patient groups. Only females with OND showed a significant correlation between responses to this peptide and responses to M. tuberculosis.

These results indicate that there is an association between proliferative responses to hsp peptides sharing sequence homology with a myelin protein, CNP, and the disease MS. The data also suggest that there can be differences in the patterns of these responses based upon MHC class II, genotype and the peptide selected. Responsiveness to some peptides may be greater depending on the presence of a specific MHC type. Results with Peptides #10 and #11, showing that only male patients with MS responded, are of additional interest. Behcet's Syndrome is an inflammatory, multi-system disease of unknown etiology that can cause inflammatory changes in CNS white matter, has a decided male preponderance, and may be associated with an infectious agent (O'Duffy; 1994; Current Opinion in Rheum., 6:39). The presence of significant responses to these peptides in males with MS provides additional evidence that immune responses to hsp may be important in MS and other inflammatory CNS diseases.

EXAMPLE 7

Induction of Tolerance to the CNP Peptide and Its Effect on EAE

EAE can be suppressed by oral administration of myelin antigens. Tolerance to the CNP 173–184 peptide will be induced and examined for the effect on development of EAE.

Induction of tolerance to CNP 173–184 peptide by exposure of Deptide to the mucosal immune system: Two methods of tolerance induction will be used:

1. induction by antigen feeding
2. induction by inhalation of antigen

These methods are selected because of their feasibility for use in a clinical situation, and for their effectiveness in ameliorating both acute and chronic EAE.

Mechanisms of tolerance vary not only with the different methods of tolerization, but are also affected by the ages of the animals (Miller et al., Eur. J. Immunol., 24:1026 (1994)) and the dosages of toleragen (Whiteacre et al., Immunol., 147:2155 (1991); Higgins et al., J. Immunol., 140:440 (1988)). Therefore, we will perform these experiments using animals of different ages, using different dosages of toleragen.

Oral tolerance: High dosages of oral toleragen induce anergy, with specificity only for the inducing peptide. Lower doses induce "bystander suppression", with effects on immune responses to other than the tolerizing antigen. In initial experiments rats of different ages will be used as well as low dosages of CNP 173–184 peptide as toleragen. Control peptide will be a hsp peptide with no sequence homology to CNP. Several such peptides have been prepared and purified.

The protocol of Miller et al., Eur. J. Immunol., 24:1026 (1994) will be followed. Ages of rats will range from neonates (24 hours of age) to adults (6–8 weeks of age), with groups separated by weekly intervals. Dosages of antigen will range from 50 $\mu$g CNP 173–184 peptide in neonates to 250 $\mu$g in adults. Since low dosages of peptide will be administered, no trypsin inhibitors will be used. Numbers of toleragen administrations will range from two to three, at intervals of 2–3 days. When young animals reach adulthood (6–8 weeks), or two days after the last feeding in adults, animals will be actively immunized with CPSC in CFA.

The course and severity of EAE will be determined.

If induced EAE is successfully modulated, adoptively transferred EAE will be modulated using the same protocol. Numbers of adoptively transferred cells will be sufficient to induce moderate (2+ severity) EAE determined as described in Example 5.

If active or adoptive EAE is modulated, chronic, relapsing EAE will be induced using the protocols described in Example 8 (CREAE). Once relapses are noted, CNP peptide or control peptide will be fed to animals using the adult protocol. The subsequent course of CREAE will be monitored.

Inhalation tolerance: The protocol of Metzler and Wraith will be followed (Metzler et al., Int. Immunol., 5:1159 (1993)). Lightly anesthetized animals of varying ages, as described above, will receive CNP 173–184 peptide or control peptide in PBS, via intra-nasal instillation. Dosages and numbers of administrations will be the same as described above for the oral tolerance protocol. When animals reach adulthood, or one to two weeks after the last intra-nasal inoculation in adults, rats will be immunized with GPSC in CFA. The onset and severity of subsequent EAE will be determined.

If actively induced EAE is modulated, adoptively transferred EAE will be similarly modified. Numbers of cells will be inoculated sufficient to induce moderate, rather than severe, disease. This number is approximately $5 \times 10^7$ cells per animal. If tolerance is successful in active or adoptive EAE, the course of chronic, relapsing EAE (CREAE) will be modulated. Relapses of EAE will be induced with CSA, using the higher dosages described by Polman et al., J. Neuroimmunol., 17:209. After at least one relapse occurs, animals will receive the adult protocol for inhalation tolerance. The frequency and severity of subsequent relapses will be monitored.

Based upon our data with immunization to CNP 173–184 peptide in IFA, it is anticipated that oral tolerance induction to this peptide will result in modulation of EAE induced by active immunization. We expect that either oral or inhalation administration of CNP-peptide will result in protection from active EAE and decreased numbers of attacks in CREAE.

EXAMPLE 8

Examination of the Effect of Immunization with CNP Peptide on Chronic or Relapsing EAE Induction of relapses in rats recovered from acute EAE: EAE in Lewis rats is usually a monophasic illness, with resistance to re-induction of disease. However, if rats are re-immunized with GPSC in CFA >30 days after recovery from acute disease, a majority of animals develop mild (1+ severity) relapses (unpublished observations). In view of these data, we will immunize young, adult, female rats with GPSC in CFA. Thirty to forty days after recovery from their acute EAE, animals will be immunized with CNP peptide in CFA or in a non-mycobacterial-containing adjuvant that nevertheless induces a DTH type immune (Allison et al., *J. Immunological Methods*, 45:157 (1986)) (e.g. SAF-1, Syntex Research, Palo Alto, Calif.). Animals will be observed for at least thirty days thereafter for the development of disease.

Alternative induction of relapses of EAE in animals with chronic, relapsing EAE (CREAE): CREAE can be induced in rats by administration of low doses of immune suppressants. Both cyclophosphamide and cyclosporin A have been used. We will induce CREAE in our animals with cyclosporin A (CSA) using a protocol modified from Polman et al (*J. Neuroimmunol.*, 17:209 (1986)). Rats will be immunized with GPSC and CFA. Concurrent with immunization, rats will be injected sub-cutaneously with low doses (0.5 mg/kg and 1 mg/kg) of CSA on an every other day schedule. These dosages are one-half to one-quarter the amounts given by Polman et al because we do not want to induce relapses with CSA alone but rather use CSA to provide a suitable immunologic environment for relapses to occur when appropriately triggered. Thus, if relapses of EAE are noted with these low dosages of CSA, the dosages will be lowered further until no spontaneous exacerbations occur. When this is achieved, CSA will be administered for 14–28 days, then animals will be immunized with CNP 173–184 peptide coupled to KLH. Control rats will consist of two groups, those that receive CSA and an hsp peptide that is not homologous with CNP, and those that receive CNP 173–184 peptide but no prior CSA treatment (only saline). After peptide immunization, CSA or saline treatment will continue and rats will be observed for at least another 30 days for the development of EAE relapses. We expect that immunization with CNP 173–184 peptide will result in decreases in relapses of CREAE.

EXAMPLE 9

HSP Peptides Can Inhibit the Development of EAE

The protocol used to determine whether a peptide had the capacity to modulate EAE was the same as that described in Example 4. Briefly 50 μg of peptide was emulsified in either CFA (supplemented with 5 mg/ml of *M. tuberculosis* H37Ra) or IFA and injected subcutaneously into one flank of female Lewis rats weighing 100–125 grams. Four weeks later animals were challenged by subcutaneous injection with 1 mg of GPSC emulsified in CFA. Severity of subsequent clinical EAE was scored using previously described criteria. Results with four different peptides are shown in FIGS. 10, 11, 12 and 13. Peptides were not coupled to KLH.

Peptide 6 has the following amino acid sequence corresponding to amino acids 195 to 209 of HSP65:

lys-gly-tyr-ile-ser-gly-tyr-phe-val-thr-asp-ala-glu-arg-gln (SEQ ID NO:11).

The results of immunization with peptide 6 are shown in FIG. 10. The results indicate that pre-immunization with Peptide #6 in IFA significantly decreases both the incidence and severity of EAE induced by immunization with GPSC.

Peptide 8 has the following amino acid sequence corresponding to amino acids 413 to 425 of HSP65:

gly-gly-val-thr-leu-leu-gln-ala-ala-pro-ala-leu-asp (SEQ ID NO:13).

The results with peptide 8 are shown in FIG. 11. The results indicate that peptide #8 confers some protection against EAE but does not protect as well as other peptides.

Peptide 9 has the following sequence corresponding to amino acids 272 to 286 of HSP65:

val-ala-val-lys-ala-pro-gly-phe-gly-asp-arg-arg-lys-ala-met (SEQ ID NO:18).

Figure 12:
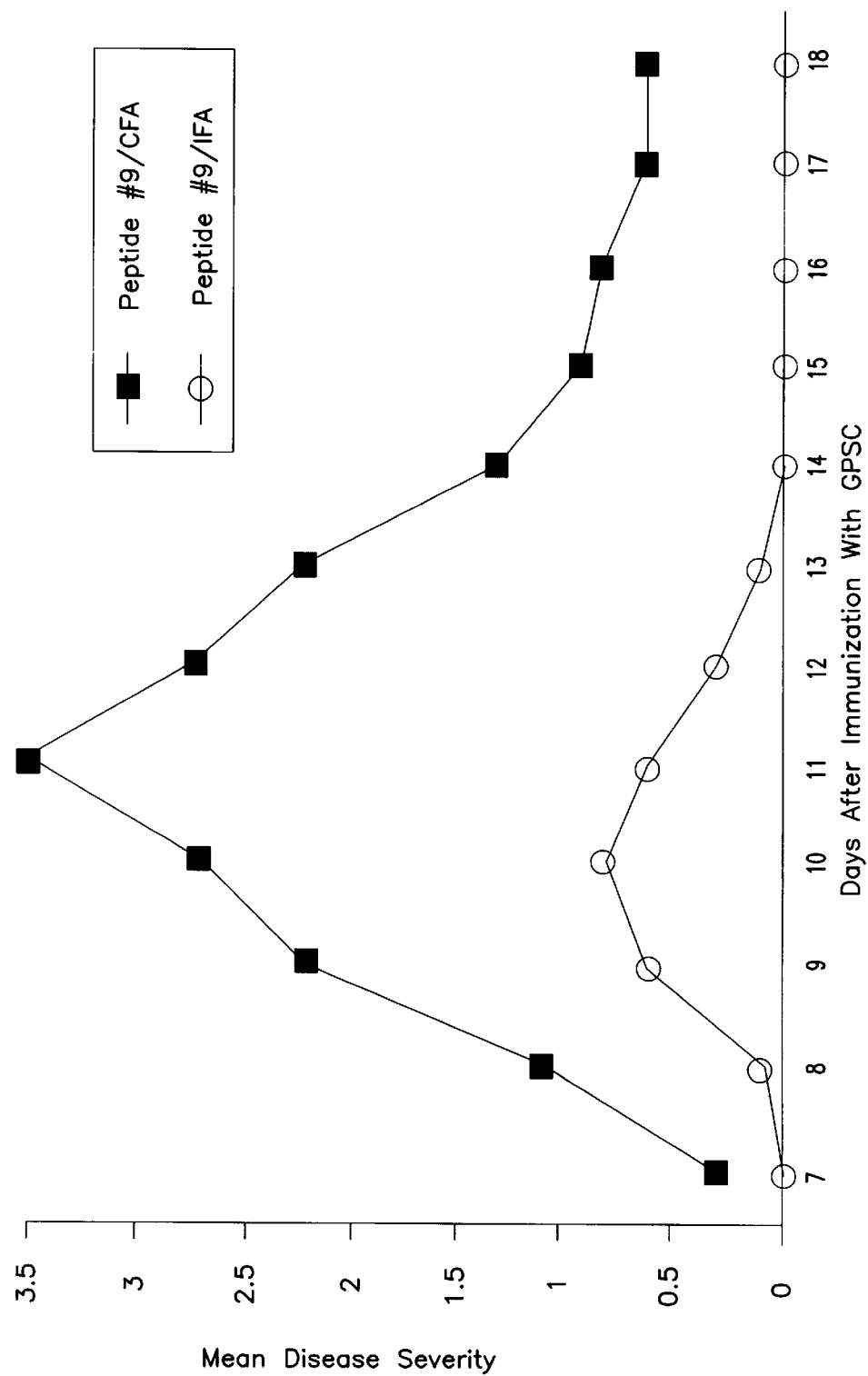
FIG. 12: Preimmunization with peptide #9 in incomplete Freund's adjuvant protects rats against EAE.

The results with peptide 9 are shown in FIG. 12. The data show that sequence homology with CNP is not necessary to protect against EAE. Other T cell epitopes of HSP65 can elicit protection.

Peptide 13 has the following sequence corresponding to amino acids 115 to 123 of HSP65:

leu-lys-arg-gly-ile-glu-lys-ala-val (SEQ ID NO:2).

Peptide 13 cross-reacts with CNP but has not been previously identified as a T cell epitope. As with the other peptides, peptide #13 was not coupled to KLH. The results shown in FIG. 13 indicate that cross-reactivity with CNP alone is not sufficient to induce protection for EAE.

In summary, certain peptides derived from HSP65 that are T cell epitopes can protect rats from developing EAE. Some of these peptides also share homology to CNP, however homology to CNP is not always necessary to provide protection against development of EAE.

EXAMPLE 10

Responses of Paired Spinal Fluid and Peripheral Blood Lymphocytes to hsp Peptides CSF lymphocytes from persons with MS or OND were examined in terms of their proliferative response to stimulation with the panel of hsp peptides described in Example 6 and shown in Table 1. These response were compared with those of peripheral blood lymphocytes (PBL) obtained concurrently from the same individuals. The patient populations are described in Table 4.

TABLE 4

Patient Populations In Which Paired CSF and Peripheral Blood Lymphocytes Were Studied

| Clinical Diagnosis and Sex | Number of Patients | Mean Age |
| --- | --- | --- |
| MS-Females | 8 | 42 years |
| MS-Males | 2 | 32 years |
| OND-Females | 6 | 53 years |
| OND-Males | 2 | 50 years |

Lymphocytes were collected from fresh CSF by centrifugation. PBL from the CSF donor were collected concurrently. Because numbers of cells in CSF were too low to allow direct assay with the antigens, these cells were expanded by culturing them with PHA-P (2 μg/ml) (Sigma Chemical Co., St. Louis, Mo.). This results in relatively non-selective stimulation of all T cells in the sample. An aliquot ($5 \times 10^4$) of concurrently collected PBL from the CSF donor were cultured in parallel with PHA-P in an analogous fashion. Cells were fed with medium containing IL-2 every 3 to 4 days and restimulated with PHA-P every 12–days. Cultures were harvested when sufficient numbers of cells were present for assay (~$3 \times 10^6$). Average time in culture before assay was 16–19 days. Proliferative responses greater than two-fold above background were considered significant. Differences in the frequencies of response to individual peptides among the different patient populations were studied using chisquares analyses. Results are shown in Table 5.

TABLE 5

Chi-Square Analyses of proliferative Responses to hsp Peptides in CSF and Peripheral Blood Lymphocytes

| Group A greater than Group B | Peptide #5 | Peptide #9 |
|---|---|---|
| MS CSF vs OND CSF | p < 0.05 | p < 0.01 |
| MS F CSF vs OND F CSF | p < 0.05 | p < 0.025 |
| MS PBL vs OND PBL | N.S. | p < 0.05 |
| MS F PBL- vs OND F PBL | N.S. | p < 0.05 |

F = females.
M = males.
N.S. = Not Significant.

These data provide further evidence that responses to specific hsp peptides are different in persons with MS compared to those with OND. In particular, they show that spinal fluid and peripheral blood T cell responses to specific hsp peptides are present in a significantly higher number of persons with MS than in control groups.

EXAMPLE 11

Specificity of Oligoclonal Bands (OCB) of Antibodies in MS Spinal Fluids

The specificity of IgG oligoclonal bands in MS CFS is not known. Oligoclonal bands in MS CSF were examined for binding to whole sonicated M. tuberculosis using isoelectric focusing.

Spinal fluids from MS patients and controls were concentrated 6–10 fold using membrane filtration techniques. Paired sera were used at a dilution of 1:100. Proteins in CSF and sera were electrophoretically separated using pre-poured ampholyte gels (Isolabs, Akron, Ohio), having a pH range of 3 to 10. Nitrocellulose membranes were prepared by incubating them for 16 hours in a solution containing sonicated, whole, M. tuberculosis, as a source of hsp. Membranes were then incubated in a suspension of skimmed milk to block any additional protein binding sites. Separated proteins on the gels were transferred to the specifically prepared nitrocellulose membranes by passive capillary absorption. In all experiments one lane of separated proteins was silver stained to determine the locations of OCB in that specimen. All strips were washed to remove unbound proteins, then the presence of IgG binding was determined using an anti-human IgG antibody and the enhanced chemiluminescence assay described in Example 5. The binding of IgG to the treated membranes was compared with the silver-stained strip showing all proteins. In this way, it could be determined if antibodies binding to M. tuberculosis proteins were present in the region of OCB.

The results show that there is very little, if any, binding of IgG from OND serum or CSF to proteins of M. tuberculosis. (data not shown) This is often the case. In the immunoaffinity blot, there are definite bands in the region of OCB in the MS CSF that bind to M. tuberculosis proteins. Binding in this region is not seen with MS serum. Thus, some oligoclonal antibodies in MS CSF bind to mycobacterial proteins.

What is claimed:

1. A method for stimulating a proliferative T-cell response for T-cells of a patient suffering from multiple sclerosis, the method comprising the step of:

administering to a patient suffering from multiple sclerosis a composition comprising isolated mycobacterial heat shock protein 65 (HSP65) or peptide which comprises an at least 9 amino acid subsequence thereof, wherein the protein or peptide is present in an amount effective to stimulate the proliferative T-cell response for T-cells of the patient.

2. The method of claim 1, wherein the HSP65 protein or peptide is immunologically cross-reactive, in an immunoblot or lymphocyte proliferation assay, with a component of myelin.

3. The method of claim 2, wherein the component of myelin is a human myelin 2',3' cyclic nucleotide phosphodiesterase.

4. The method of claim 1, wherein the HSP65 protein or peptide comprises the sequence:

Ly-Gly-Tyr-Ile-Ser-Gly-Try-Phe-Val-Thr-Asp-Ala Glu-Arg-Gln(SEQ ID NO:11);

Gly-Gly-Val-Thr-Leu-Leu-Gln-Ala-Ala-Pro-Ala-Leu-Asp (SEQ ID NO: 13);

Val-Ala-Val-Lys-Ala-Pro-Gly-Phe-Gly-Asp-Arg-Arg-Lys-Ala-Met (SEQ ID NO: 18);

or a combination thereof.

5. The method of claim 1, wherein the HSP65 protein or peptide comprises the sequence:

Leu-Lys-Pro-Gly-Leu-Glu-Lys-Asp-Phe (SEQ ID NO: 1).

6. The method of claim 1, wherein the HSP65 protein or peptide consists of the sequence:

Lys-Gly-Tyr-Ile-Ser-Gly-Try-Phe-Val-Thr-Asp-Ala-Glu-Arg-Gln (SEQ ID NO:11);

Gly-Gly-Val-Thr-Leu-Leu-Gln-Ala-Ala-Pro-Ala-Leu-Asp (SEQ ID NO: 13);

Val-Ala-Val-Lys-Ala-Pro-Gly-Phe-Gly-Asp-Arg Arg-Lys-Ala-Met (SEQ ID NO: 18);

or a combination thereof.

7. The method of claim 1, wherein the HSP65 protein or peptide consists of the sequence:

Leu-Lys-Pro-Gly-Leu-Glu-Lys-Asp-Phe (SEQ ID NO: 1).

8. The method of claim 1, wherein the patient's T-cells are stimulated to proliferate to an extent more than 2-fold greater than the patient's T-cells in the absence of the HSP65 protein or peptide.

9. The method of claim 1, wherein the patient's T-cells are stimulated to proliferate to an extent more than 3-fold greater than the patient's T-cells in the absence of the HSP65 protein or peptide.

10. A method for stimulating a proliferative T-cell response for T-cells of a patient suffering from multiple sclerosis, the method comprising the steps of:

administering to a patient suffering from multiple sclerosis a composition comprising isolated mycobacterial heat shock protein 65 (HSP65) or peptide which comprises an at least 9 amino acid subsequence thereof, wherein the protein or peptide is present in an amount effective to stimulate the proliferative T-cell response for T-cells of the patient, and wherein the HSP65 protein or peptide is immunologically crossreactive in an immunoblot or lymphocyte proliferation assay with a component of myelin; and stimulating the proliferative T-cell response for T-cells of the patient, wherein the patients's T-cells are stimulated to proliferate to an extent more than 2-fold greater than the patient's T-cells in the absence of the HSP65 protein or peptide.

11. The method of claim 10, wherein the component of myelin is a human myelin 2',3' cyclic nucleotide phosphodiesterase.

12. The method of claim 10, wherein the HSP65 protein or peptide comprises the sequence:

Lys-Gly-Tyr-Ile-Ser-Gly-Try-Phe-Val-Thr-Asp-Ala-Glu-Arg-Gln ( SEQ ID NO: 11);

Gly-Gly-Val-Thr-Leu-Leu-Gln-Ala-Ala-Pro-Ala-Leu-Asp (SEQ ID NO: 13);

Val-Ala-Val-Lys-Ala-Pro-Gly-Phe-Gly-Asp-Arg-Arg-Lys-Ala-Met (SEQ ID NO: 18);

or a combination thereof.

13. The method of claim 10, wherein the HSP65 protein or peptide comprises the sequence:

Leu-Lys-Pro-Gly-Leu-Glu-Lys-Asp-Phe (SEQ ID NO: 1).

14. The method of claim 10, wherein the patient's T-cells are stimulated to proliferate to an extent more than 3-fold greater than the patient's T-cells in the absence of the HSP65 protein or peptide.

15. A method for stimulating a proliferative T-cell response for T-cells of a patient suffering from multiple sclerosis, the method comprising the steps of:

administering to a patient suffering from multiple sclerosis a composition comprising isolated mycobacterial heat shock protein 65 (HSP65) or peptide which comprises an at least 9 amino acid subsequence thereof, wherein the protein or peptide is present in an amount effective to stimulate the proliferative T-cell response for T-cells of the patient, and wherein the HSP65 protein or peptide comprises the sequence Lys-Gly-Tyr-Ile-Ser-Gly-Try-Phe-Val-Asp-Ala-Glu-Arg-Gln (SEQ ID No. 11), Gly-Gly-Val-Thr-Leu-Leu-Gln-Ala-Ala-Pro-Ala-Leu-Asp (SEQ ID No. 13), Val-Ala-Val-Lys-Ala-Pro-Gly-Phe-Gly-Asp-Arg-Lys-Ala-Met (SEQ ID No. 18), Leu-Lys-Pro-Gly-Leu-Glu-Lys-Asp-Phe (SEQ ID No. 1), or combination thereof; and stimulating the proliferative T-cell response for T-cells of the patient, wherein the patients's T-cells are stimulated to proliferate to an extent more than 2-fold greater than the patient's T-cells in the absence of the HSP65 protein or peptide.

* * * * *